(12) United States Patent
Griesgraber et al.

(10) Patent No.: US 12,024,514 B2
(45) Date of Patent: Jul. 2, 2024

(54) N-1 BRANCHED ALKYL ETHER SUBSTITUTED IMIDAZO[4,5-C]QUINOLINE COMPOUNDS, COMPOSITIONS, AND METHODS

(71) Applicant: Solventum Intellectual Properties Company, Maplewood, MN (US)

(72) Inventors: George W. Griesgraber, Eagan, MN (US); Bryon A. Merrill, River Falls, WI (US); Michael J. Rice, Woodbury, MN (US)

(73) Assignee: Solventum Intellectual Properties Company, Maplewood, MN (US)

(*) Notice: Subject to any disclaimer, the term of this patent is extended or adjusted under 35 U.S.C. 154(b) by 558 days.

(21) Appl. No.: 17/309,216

(22) PCT Filed: Nov. 11, 2019

(86) PCT No.: PCT/IB2019/059666
§ 371 (c)(1),
(2) Date: May 7, 2021

(87) PCT Pub. No.: WO2020/109898
PCT Pub. Date: Jun. 4, 2020

(65) Prior Publication Data
US 2021/0323962 A1    Oct. 21, 2021

Related U.S. Application Data

(60) Provisional application No. 62/771,229, filed on Nov. 26, 2018.

(51) Int. Cl.
C07D 471/04 (2006.01)
A61K 31/4745 (2006.01)
A61P 37/04 (2006.01)

(52) U.S. Cl.
CPC ........ *C07D 471/04* (2013.01); *A61K 31/4745* (2013.01); *A61P 37/04* (2018.01)

(58) Field of Classification Search
CPC .... C07D 471/04; A61P 37/04; A61K 31/4745
See application file for complete search history.

(56) References Cited

U.S. PATENT DOCUMENTS

| | | | |
|---|---|---|---|
| 3,700,674 A | 10/1972 | Diehl | |
| 4,689,338 A | 8/1987 | Gerster | |
| 5,352,784 A | 10/1994 | Nikolaides | |
| 5,389,640 A | 2/1995 | Gerster | |
| 5,446,153 A | 8/1995 | Lindstrom | |
| 6,039,969 A | 3/2000 | Tomai | |
| 6,110,929 A | 8/2000 | Gerster | |
| 6,194,425 B1 | 2/2001 | Gerster | |
| 6,200,592 B1 | 3/2001 | Tomai | |
| 6,331,539 B1 | 12/2001 | Crooks | |
| 6,451,810 B1 | 9/2002 | Coleman | |
| 6,664,264 B2 | 12/2003 | Dellaria | |
| 7,544,697 B2 | 6/2009 | Hays | |
| 7,915,281 B2 | 3/2011 | Moser | |
| 7,923,560 B2 | 4/2011 | Wightman | |
| 7,943,609 B2 | 5/2011 | Griesgraber | |
| 8,088,790 B2 | 1/2012 | Kshirsagar | |
| 8,350,034 B2 | 1/2013 | Griesgraber | |
| 8,673,932 B2 | 3/2014 | Kshirsagar | |
| 8,691,837 B2 | 4/2014 | Krepski | |
| 8,697,873 B2 | 4/2014 | Krepski | |
| 2003/0212092 A1* | 11/2003 | Heppner | A61P 31/12 546/82 |
| 2005/0267145 A1 | 12/2005 | Merrill | |

FOREIGN PATENT DOCUMENTS

WO    WO 2002-046193    6/2002

OTHER PUBLICATIONS

Berge, "Pharmaceutical Salts", Journal of Pharmaceutical Sciences, 1977, vol. 66, No. 01, pp. 1-19.
Gübitz, "Chiral Separation by Chromatographic and Electromigration Techniques. A Review", Biopharmaceutics and Drug Disposition, 2001, vol. 22, pp. 291-336.
Higuchi, et al., "Pro-drugs as Novel Delivery Systems", vol. 14 of the ACS Symposium Series, pp. 1-6.
Liu, "Highly Chemoselective O-Ethylation of N-Boc Amino Alcohols Using Phase Transfer Catalysis", Organic Process Research & Development, 2014, vol. 18, No. 09, pp. 1142-1144.
Mane, "Racemic Drug Resolution: A Comprehensive Guide", Analytical Methods, 2016, vol. 08, pp. 7567-7586.
Okamoto, "Chiral HPLC For Efficient Resolution of Enantiomers", Chemical Society Reviews, 2008, vol. 37, pp. 2593-2608.
Schiaffo, "Structure-Activity Relationship Analysis of Imidazoquinolines with Toll-Like Receptors 7 and 8 Selectivity and Enhanced Cytokine Induction", Journal of Medicinal Chemistry, 2014, vol. 57, pp. 339-347.
Williams, "Grignard Reactions to Chiral Oxazolidine Aldehydes", Tetrahedron, 1996, vol. 52, No. 36, pp. 11673-11694.
International Search Report for PCT International Application No. PCT/IB2019/059666, dated Jan. 7, 2020, 6 pages.

* cited by examiner

*Primary Examiner* — Jeffrey S Lundgren
*Assistant Examiner* — Ibrahim D Bori
(74) *Attorney, Agent, or Firm* — Ashley M. Dreis

(57) ABSTRACT

Imidazo[4,5-c]quinoline compounds having a substituent that is attached at the N-1 position by a branched group, single enantiomers of the compounds, pharmaceutical compositions containing the compounds, and methods of making the compounds are disclosed. Methods of use of the compounds as immune response modifiers, for inducing cytokine biosynthesis in humans and animals, and in the treatment of diseases including infectious and neoplastic diseases are also disclosed.

22 Claims, No Drawings

N-1 BRANCHED ALKYL ETHER SUBSTITUTED IMIDAZO[4,5-C]QUINOLINE COMPOUNDS, COMPOSITIONS, AND METHODS

CROSS REFERENCE TO RELATED APPLICATIONS

This application is a national stage filing under 35 U.S.C. 371 of PCT/IB2019/059666, filed Nov. 11, 2019, which claims the benefit of Provisional Application No. 62/771,229, filed Nov. 26, 2018, the disclosure of which is incorporated by reference in its/their entirety herein.

BACKGROUND

Some drug compounds act by stimulating certain key aspects of the immune system, as well as by suppressing certain other aspects (e.g., U.S. Pat. No. 6,039,969 (Tomai et al.) and U.S. Pat. No. 6,200,592 (Tomai et al.)). These compounds are sometimes referred to as immune response modifiers (IRMs). Some IRM compounds are useful for treating viral diseases, neoplasias, and $T_H2$-mediated diseases. Some IRM compounds are useful as vaccine adjuvants.

IRM compounds have been reported based on the following bicyclic and tricyclic ring systems: 1H-imidazo[4,5-c]quinolin-4-amines (e.g., U.S. Pat. No. 4,689,338 (Gerster)); 1H-imidazo[4,5-c]pyridin-4-amines (e.g., U.S. Pat. No. 5,446,153 (Lindstrom et al.)); 1H-imidazo[4,5-c][1,5]naphthyidin-4-amines (e.g., U.S. Pat. No. 6,194,425 (Gerster et al.)); thiazolo[4,5-c]quinolone-4-amines and oxazolo[4,5-c]quinolone-4-amines (e.g., U.S. Pat. No. 6,110,929 (Gerster et al.)); 6,7,8,9-1H-tetrahydro-1H-imidazo[4,5-c]quinolin-4-amines (e.g., U.S. Pat. No. 5,352,784 (Nikolaides et al.)); 2H-pyrazolo[3,4-c]quinolone-4-amines (e.g., U.S. Pat. No. 7,544,697 (Hays et al.)); and N–1 and 2-substituted 1H-imidazo[4,5-c]quinolin-4-amines (e.g., U.S. Pat. No. 6,331,539 (Crooks et al.), U.S. Pat. No. 6,451,810 (Coleman et al.), U.S. Pat. No. 6,664,264 (Dellaria et al.), U.S. Pat. No. 8,691,837 (Krepski et al.), U.S. Pat. No. 8,088,790 (Kshirsagar et al.), U.S. Pat. No. 8,673,932 (Kshirsagar et al.), U.S. Pat. No. 8,697,873 (Krepski et al.), and U.S. Pat. No. 7,915,281 (Krepski et al.)).

SUMMARY

New compounds, salts thereof, and compositions including such compounds and salts that can be useful, for example, in inducing cytokine biosynthesis in humans and animals are disclosed. Such compounds are of the following Formula (I):

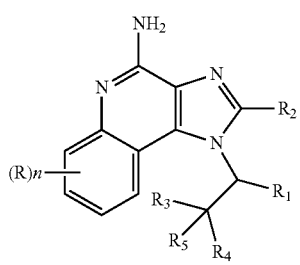

Formula (I)

wherein:
n is an integer of 0 or 1;
R is selected from the group consisting of halogen, hydroxy, alkyl, alkoxy, and —C(O)—O— alkyl;
$R_1$ is —X—O—Y where X is a $C_{1-3}$ alkylene and Y is a $C_{1-3}$ alkyl;
$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$;
$R_3$ is a $C_{1-4}$alkyl, $R_4$ is a $C_{1-4}$alkyl, or $R_3$ and $R_4$ are combined to form a ring of 3-7 carbon atoms optionally having one oxygen atom in the ring; and
$R_5$ is —H, —CH$_3$, —F, or —OH.

The compounds of Formula (I), and salts thereof, have a chiral center in the branched group off N–1. Thus, the compounds of Formula (I), and salts thereof, can be resolved, and/or synthesized using well-known techniques and chiral starting materials, into compounds of Formulas (II) and (III), and salts thereof:

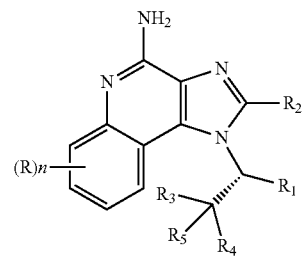

Formula (II)

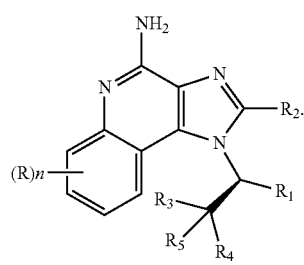

Formula (III)

The compounds and salts, such as pharmaceutically acceptable salts, of these compounds can be used as immune response modifiers due to their ability to induce cytokine biosynthesis (e.g., induce the synthesis of at least one cytokine) and otherwise modulate the immune response when administered to humans or animals. The compounds and salts thereof can therefore be used in the treatment of a variety of conditions such as viral diseases and tumors that are responsive to such changes in the immune response. The compounds and salts thereof can also be used as vaccine adjuvants when administered in combination with a vaccine.

Herein, when embodiments of Formulas (I), (II), and (III) are described, it is generally assumed that such statements refer to the compounds as well as the salts thereof.

Pharmaceutical compositions containing an effective amount of a compound (or salts thereof including pharmaceutically acceptable salts thereof) of Formula (I), such as a compound of Formula (II), Formula (III), or a combination thereof, are disclosed.

Also disclosed are methods of inducing cytokine biosynthesis in a human or animal, treating a viral disease in a human or animal, and treating a neoplastic disease in a human or animal by administering to the human or animal a compound of Formula (I), such as a compound of Formula (II), Formula (III), or a combination thereof, and/or pharmaceutically acceptable salt thereof.

The term "alkyl" refers to a monovalent group that is a radical of an alkane and includes straight-chain, branched, cyclic, and bicyclic alkyl groups, and combinations thereof. Unless otherwise indicated, the alkyl groups typically contain from 1 to 20 carbon atoms. In some embodiments, the alkyl groups contain 1 to 12 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atom s, 1 to 3 carbon atom s, or 1 to 2 carbon atoms. Examples of "alkyl" groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkylene" refers to a divalent group that is a radical of an alkane and includes groups that are linear, branched, cyclic, bicyclic, or a combination thereof. Unless otherwise indicated, the alkylene group typically has 1 to 20 carbon atoms. In some embodiments, the alkylene group has 1 to 12 carbon atoms, 1 to 10 carbon atoms, 1 to 9 carbon atoms, 1 to 8 carbon atoms, 1 to 7 carbon atoms, 1 to 6 carbon atoms, 1 to 5 carbon atoms, 1 to 4 carbon atoms, 1 to 3 carbon atom s, or 1 to 2 carbon atoms. Examples of "alkylene" groups include methylene, ethylene, propylene, 1,4-butylene, 1,4-cyclohexylene, and 1,4-cyclohexyldimethylene.

The term "alkoxy" refers to a monovalent group having an oxy group bonded directly to an alkyl group.

The term "$C_{x-y}$alkyl" and "$C_{x-y}$alkoxy" are inclusive of straight chain groups, branched chain groups, cyclic groups, and combinations thereof that have X to Y carbon atoms. For example, a "$C_{1-5}$alkyl" includes alkyl groups of 1 carbon, 2 carbons, 3 carbons, 4 carbons, or 5 carbons. Some examples of "$C_{1-5}$alkyl" include methyl, ethyl, n-propyl, isopropyl, n-butyl, sec-butyl, isobutyl, isomeric pentyls, cyclopropyl, cyclopentyl, and —$CH_2$-cyclopropyl.

The "salt" of a compound includes pharmaceutically acceptable salts, such as those described in Berge, Stephen M., "Pharmaceutical Salts," *Journal of Pharmaceutical Sciences*, 1977, 66, pages 1-19. For example, salts can be prepared by reacting a free base compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluene sulfonic acid, salicylic acid, succinic acid, tartaric acid, citric acid, pamoic acid, xinafoic acid, oxalic acid, and the like. Typical pharmaceutically acceptable salts include hydrochloride and dihydrochloride.

As used herein, "pharmaceutically acceptable carriers" include those carriers that can deliver therapeutically or prophylactically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, 18$^{th}$ Edition (1990), Mack Publishing Co. and can be readily selected by one of ordinary skill in the art.

"Effective amount" (including "therapeutically effective amount" and "prophylactically effective amount") are defined as an amount of compound or salt sufficient to induce a therapeutic or prophylactic effect, such as cytokine induction, immunomodulation, antitumor activity, and/or antiviral activity. Depending on the disease or condition, the desired cytokine profile, and/or the acceptable level of side effects, the effective amount may vary. For example, a small amount of a very active compound or salt, or a large amount of a compound or salt of low activity, may be used to avoid undesirable side effects.

"Treat" and "treatment" as well as variations thereof refer to reducing, limiting progression, ameliorating, preventing, or resolving to any extent the symptoms or signs related to a condition.

"Ameliorate" and "ameliorating" refers to any reduction in the extent, severity, frequency, and/or likelihood of a symptom or clinical characteristic of a particular disease or condition.

"Antigen" refers to any substance that can be bound by an antibody in a manner that is immunospecific to some degree.

Herein, the term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether they materially affect the activity or action of the listed elements. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof).

The words "preferred" and "preferably" refer to embodiments of the disclosure that may afford certain benefits, under certain circumstances. However, other claims may also be preferred, under the same or other circumstances. Furthermore, the recitation of one or more preferred claims does not imply that other claims are not useful and is not intended to exclude other claims from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the terms "ambient temperature" or "room temperature" refers to a temperature of 20° C. to 25° C. or 22° C. to 25° C.

The term "in the range" or "within a range" (and similar statements) includes the endpoints of the stated range.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

When a group is present more than once in a formula described herein, each group is "independently" selected, whether specifically stated or not. For example, when more than one R group is present in a formula, each R group is independently selected.

Reference throughout this specification to "one embodiment," "an embodiment," "certain embodiments," or "some embodiments," etc., means that a feature, configuration, composition, or characteristic described in connection with the embodiment is included in at least one embodiment of the invention. Thus, the appearances of such phrases in various places throughout this specification are not necessarily referring to the same embodiment of the invention. Furthermore, the features, configurations, compositions, or characteristics may be combined in any suitable manner in one or more embodiments.

The above summary of the present disclosure is not intended to describe each disclosed embodiment or every implementation of the present invention. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

DETAILED DESCRIPTION OF ILLUSTRATIVE EMBODIMENTS

This disclosure provides compounds (and salts thereof) of the following Formula (I):

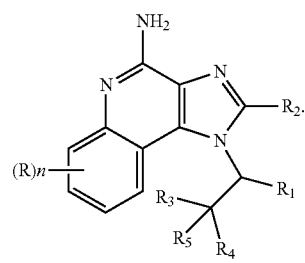

Formula (I)

The compounds of Formula (I), and salts thereof, have a chiral center in the branched group off N-1. Thus, the compounds of Formula (I), and salts thereof, can be resolved, and/or synthesized using well-known techniques and chiral starting materials, into compounds of Formulas (II) and (III), and salts thereof:

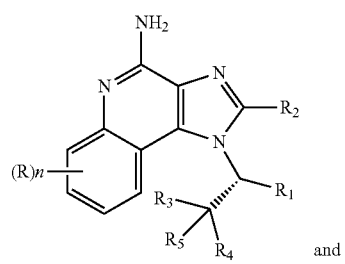

Formula (II)

and

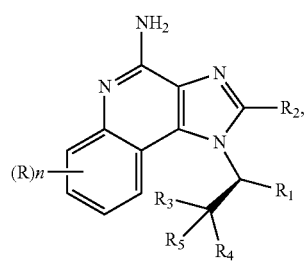

Formula (III)

wherein:
  n is an integer of 0 or 1;
  R is selected from the group consisting of halogen, hydroxy, alkyl, alkoxy, and —C(O)—O— alkyl;
  $R_1$ is —X—O—Y where X is a $C_{1-3}$alkylene and Y is a $C_{1-3}$alkyl;
  $R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$;
  $R_3$ is a $C_{1-4}$alkyl, $R_4$ is a $C_{1-4}$alkyl, or $R_3$ and $R_4$ are combined to form a ring of 3-7 carbon atoms optionally having one oxygen atom in the ring; and
  $R_5$ is —H, —CH$_3$, —F, or —OH.

Depending on the disease or condition, the desired cytokine profile, and/or the acceptable level of side effects, a compound of Formula (I), or salt thereof, may be more desirable than another compound of Formula (I), or salt thereof. Generally, a more active compound or salt of Formula (I) would be desirable for use in treating a viral disease, for example, whereas a less active compound of Formula (I), or salt thereof, may be used in certain situations, for example, to avoid undesirable side effects and/or for treating sensitive areas (e.g., mucous membranes). Compounds or salts thereof that are inactive toward cytokine production (e.g., the compound of Example 6) may be suitable in the treatment, e.g., of autoimmune conditions as a result of inhibiting cytokine biosynthesis.

In some embodiments of Formulas (I), (II), and (III), R is selected from the group consisting of halogen, hydroxy, —$C_{1-12}$alkyl, —$C_{1-12}$alkoxy, and —C(O)—O—$C_{1-10}$alkyl. In some embodiments of Formulas (I), (II), and (III), R is selected from the group consisting of halogen, hydroxy, —$C_{1-7}$alkyl, —$C_{1-7}$alkoxy, and —C(O)—O—$C_{1-5}$alkyl. In some embodiments of Formulas (I), (II), and (III), R is selected from the group consisting of hydroxy, F, and Cl. In some embodiments of Formulas (I), (II), and (III), R is selected from the group consisting of F and Cl.

In some embodiments of Formulas (I), (II), and (III), n is 0.

In some embodiments of Formulas (I), (II), and (III), $R_1$ is —X—O—Y where X is —$CH_2$—, —$CH_2CH_2$—, or —$CH(CH_3)$— and Y is a $C_{1-3}$alkyl. In some embodiments of Formulas (I), (II), and (III), X is —$CH_2$— or —$CH(CH_3)$—. In some embodiments of Formulas (I), (II), and (III), Y is —$CH_3$ or —$CH_2CH_3$.

In some embodiments of Formulas (I), (II), and (III), $R_2$ is selected from the group consisting of hydrogen, methyl, and ethyl.

In some embodiments of Formulas (I), (II), and (III), $R_3$ is a $C_{1-4}$alkyl. In some embodiments of Formulas (I), (II), and (III), $R_3$ is methyl or ethyl. In some embodiments of Formulas (I), (II), and (III), $R_4$ is a $C_{1-4}$alkyl. In some embodiments of Formulas (I), (II), and (III), $R_4$ is methyl or ethyl. In some embodiments of Formulas (I), (II), and (III), $R_3$ and $R_4$ are each methyl. In some embodiments of Formulas (I), (II), and (III), $R_3$ and $R_4$ are each ethyl.

In some embodiments of Formulas (I), (II), and (III), $R_3$ and $R_4$ are combined to form a ring of 3-7 carbon atoms optionally having one oxygen atom in the ring. In some embodiments of Formulas (I), (II), and (III), $R_3$ and $R_4$ are combined to form a ring of 3-7 carbon atoms. In some embodiments of Formulas (I), (II), and (III), $R_3$ and $R_4$ are combined to form a ring of 3-7 carbon atoms having one oxygen atom in the ring.

In some embodiments of Formulas (I), (II), and (III), $R_5$ is —H, —$CH_3$, or —OH.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is selected from the group consisting of hydrogen, methyl, and ethyl; $R_3$ is a $C_{1-4}$alkyl; $R_4$ is a $C_{1-4}$alkyl; $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is selected from the group consisting of hydrogen, methyl, and ethyl; $R_3$ is methyl or ethyl; $R_4$ is methyl or ethyl; $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is hydrogen; $R_3$ is methyl or ethyl; $R_4$ is methyl or ethyl; $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is hydrogen; $R_3$ is methyl or ethyl; $R_4$ is methyl or ethyl; $R_5$ is —OH; and n is 0. Examples of such compounds include:
(3R)-3-(4-aminoimidazo[4,5-c]quinolin-1-yl)-4-ethoxy-2-methyl-butan-2-ol (Example 5);
(3S)-3-(4-aminoimidazo[4,5-c]quinolin-1-yl)-4-ethoxy-2-methyl-butan-2-ol (Example 6);
(2R)-2-(4-aminoimidazo[4,5-c]quinolin-1-yl)-1-ethoxy-3-ethyl-pentan-3-ol (Example 12); and
(3R,4S)-3-(4-aminoimidazo[4,5-c]quinolin-1-yl)-4-ethoxy-2-methyl-pentan-2-ol (Example 13).

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is hydrogen; $R_3$ is methyl or ethyl; $R_4$ is methyl or ethyl; $R_5$ is —$CH_3$; and n is 0. Examples of such compounds include:
1-[(1S)-1-(ethoxymethyl)-2,2-dimethyl-propyl]imidazo[4,5-c]quinolin-4-amine (Example 9);
1-[(1R)-1-(ethoxymethyl)-2,2-dimethyl-propyl]imidazo[4,5-c]quinolin-4-amine (Example 10); and
1-[(1S)-1-(methoxymethyl)-2,2-dimethyl-propyl]imidazo[4,5-c]quinolin-4-amine (Example 11).

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is hydrogen; $R_3$ is methyl or ethyl; $R_4$ is methyl or ethyl; $R_5$ is —H; and n is 0. Examples of such compounds include:
1-[(1S)-1-(ethoxymethyl)-2-methyl-propyl]imidazo[4,5-c]quinolin-4-amine (Example 1); and
1-[(1R)-1-(ethoxymethyl)-2-methyl-propyl]imidazo[4,5-c]quinolin-4-amine (Example 2).

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is methyl; $R_3$ is methyl or ethyl; $R_4$ is methyl or ethyl; and $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is methyl; $R_3$ is methyl or ethyl; $R_4$ is methyl or ethyl; $R_5$ is —H; and n is 0. Examples of such compounds include:
1-[(1S)-1-(ethoxymethyl)-2-methyl-propyl]-2-methyl-imidazo[4,5-c]quinolin-4-amine (Example 3); and 1-[(1R)-1-(ethoxymethyl)-2-methyl-propyl]-2-methyl-imidazo[4,5-c]quinolin-4-amine (Example 4).

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is methyl; $R_3$ is methyl or ethyl; $R_4$ is methyl or ethyl; $R_5$ is —OH; and n is 0. An example of such compounds includes:
(3R)-3-(4-amino-2-methyl-imidazo[4,5-c]quinolin-1-yl)-4-ethoxy-2-methyl-butan-2-ol (Example 7).

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is ethyl; $R_3$ is methyl or ethyl; $R_4$ is methyl or ethyl; $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is ethyl; $R_3$ is methyl or ethyl; $R_4$ is methyl or ethyl; $R_5$ is —OH; and n is 0. An example of such compounds includes:
(3R)-3-(4-amino-2-ethyl-imidazo[4,5-c]quinolin-1-yl)-4-ethoxy-2-methyl-butan-2-ol (Example 8).

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is selected from the group consisting of hydrogen, methyl, and ethyl; $R_3$ and $R_4$ are combined to form a ring of 3-7 carbon atoms optionally having one oxygen atom in the ring; $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is hydrogen; $R_3$ and $R_4$ are combined to form a ring of 3-7 carbon atoms optionally having one oxygen atom in the ring; $R_5$ is —H, —$CH_3$, or —OH; and n is 0.

In some embodiments of Formulas (I), (II), and (III), $R_1$ is —X—O—Y where X is —$CH_2$— or —$CH(CH_3)$— and Y is —$CH_3$ or —$CH_2CH_3$; $R_2$ is hydrogen; $R_3$ and $R_4$ are combined to form a ring of 3-7 carbon atoms optionally having one oxygen atom in the ring; $R_5$ is —OH; and n is 0. An example of such compounds includes:

1-[(1R)-1-(4-aminoimidazo[4,5-c]quinolin-1-yl)-2-ethoxyethyl]cyclopentanol (Example 14).

In some embodiments of Formulas (I), (II), and (III), the compound is present in the form of a salt. The salt is typically a pharmaceutically acceptable salt. Most commonly the salt is a hydrochloride salt.

In some embodiments, mixtures of enantiomeric compounds, or salts thereof, of Formulas (II) and (III) are present.

In some embodiments, the compound of Formula (II), or salt thereof, has an enantiomeric purity of at least 80% enantiomeric excess (80% ee). The enantiomeric purity of a compound of Formula (II), or salt thereof, is relative to a compound of Formula (III), or salt thereof. In some embodiments, the compound of Formula (II), or salt thereof, has an enantiomeric purity of at least 90% enantiomeric excess (90% ee). In some embodiments, the compound of Formula (II), or salt thereof, has an enantiomeric purity of at least 95% enantiomeric excess (95% ee). In some embodiments, the compound of Formula (II), or salt thereof, has an enantiomeric purity of at least 97% enantiomeric excess (97% ee). In some embodiments, the compound of Formula (II), or salt thereof, has an enantiomeric purity of at least 98% enantiomeric excess (98% ee). In some embodiments, the compound of Formula (II), or salt thereof, has an enantiomeric purity of at least 99% enantiomeric excess (99% ee). In some embodiments, the compound of Formula (II), or salt thereof, has an enantiomeric purity of at least 99.5% enantiomeric excess (99.5% ee). In some embodiments, the compound of Formula (II), or salt thereof, has an enantiomeric purity of at least 99.8% enantiomeric excess (99.8% ee).

In some embodiments, the compound of Formula (III), or salt thereof, has an enantiomeric purity of at least 80% enantiomeric excess (80% ee). The enantiomeric purity of a compound of Formula (III), or salt thereof, is relative to a compound of Formula (II), or salt thereof. In some embodiments, the compound of Formula (III), or salt thereof, has an enantiomeric purity of at least 90% enantiomeric excess (90% ee). In some embodiments, the compound of Formula (III), or salt thereof, has an enantiomeric purity of at least 95% enantiomeric excess (95% ee). In some embodiments, the compound of Formula (III), or salt thereof, has an enantiomeric purity of at least 97% enantiomeric excess (97% ee). In some embodiments, the compound of Formula (III), or salt thereof, has an enantiomeric purity of at least 98% enantiomeric excess (98% ee). In some embodiments, the compound of Formula (III), or salt thereof, has an enantiomeric purity of at least 99% enantiomeric excess (99% ee). In some embodiments, the compound of Formula (III), or salt thereof, has an enantiomeric purity of at least 99.5% enantiomeric excess (99.5% ee). In some embodiments, the compound of Formula (III), or salt thereof, has an enantiomeric purity of at least 99.8% enantiomeric excess (99.8% ee).

Exemplary compounds of Formulas (I), (II), and (III) are presented in Tables 1-21. In the Tables 1-21, each row represents a specific compound with n, $R_1$; $R_2$, $R_3$, $R_4$, and $R_5$ defined.

TABLE 1

| n | $R_1$ | $R_2$ | $R_3$ | $R_4$ | $R_5$ |
|---|---|---|---|---|---|
| 0 | —$CH_2$—O—$CH_3$ | —H | —$CH_3$ | —$CH_3$ | —H |
| 0 | —$CH_2$—O—$CH_2CH_3$ | —H | —$CH_3$ | —$CH_3$ | —H |
| 0 | —$CH(CH_3)$—O—$CH_3$ | —H | —$CH_3$ | —$CH_3$ | —H |
| 0 | —$CH(CH_3)$—O—$CH_2CH_3$ | —H | —$CH_3$ | —$CH_3$ | —H |
| 0 | —$CH_2CH_2$—O—$CH_3$ | —H | —$CH_3$ | —$CH_3$ | —H |
| 0 | —$CH_2CH_2$—O—$CH_2CH_3$ | —H | —$CH_3$ | —$CH_3$ | —H |

TABLE 2

| n | $R_1$ | $R_2$ | $R_3$ | $R_4$ | $R_5$ |
|---|---|---|---|---|---|
| 0 | —$CH_2$—CO—$CH_3$ | —$CH_3$ | —$CH_3$ | —$CH_3$ | —H |
| 0 | —$CH_2$—O—$CH_2CH_3$ | —$CH_3$ | —$CH_3$ | —$CH_3$ | —H |
| 0 | —$CH(CH_3)$—O—$CH_3$ | —$CH_3$ | —$CH_3$ | —$CH_3$ | —H |
| 0 | —$CH(CH_3)$—O—$CH_2CH_3$ | —$CH_3$ | —$CH_3$ | —$CH_3$ | —H |
| 0 | —$CH_2CH_2$—O—$CH_3$ | —$CH_3$ | —$CH_3$ | —$CH_3$ | —H |
| 0 | —$CH_2CH_2$—O—$CH_2CH_3$ | —$CH_3$ | —$CH_3$ | —$CH_3$ | —H |

TABLE 3

| n | $R_1$ | $R_2$ | $R_3$ | $R_4$ | $R_5$ |
|---|---|---|---|---|---|
| 0 | —$CH_2$—O—$CH_3$ | —$CH_2CH_3$ | —$CH_3$ | —$CH_3$ | —H |
| 0 | —$CH_2$—O—$CH_2CH_3$ | —$CH_2CH_3$ | —$CH_3$ | —$CH_3$ | —H |
| 0 | —$CH(CH_3)$—O—$CH_3$ | —$CH_2CH_3$ | —$CH_3$ | —$CH_3$ | —H |
| 0 | —$CH(CH_3)$—O—$CH_2CH_3$ | —$CH_2CH_3$ | —$CH_3$ | —$CH_3$ | —H |
| 0 | —$CH_2CH_2$—O—$CH_3$ | —$CH_2CH_3$ | —$CH_3$ | —$CH_3$ | —H |
| 0 | —$CH_2CH_2$—O—$CH_2CH_3$ | —$CH_2CH_3$ | —$CH_3$ | —$CH_3$ | —H |

TABLE 4

| n | $R_1$ | $R_2$ | $R_3$ | $R_4$ | $R_5$ |
|---|---|---|---|---|---|
| 0 | —$CH_2$—O—$CH_3$ | —H | —$CH_2CH_3$ | —$CH_3$ | —H |
| 0 | —$CH_2$—O—$CH_2CH_3$ | —H | —$CH_2CH_3$ | —$CH_3$ | —H |
| 0 | —$CH(CH_3)$—O—$CH_3$ | —H | —$CH_2CH_3$ | —$CH_3$ | —H |
| 0 | —$CH(CH_3)$—O—$CH_2CH_3$ | —H | —$CH_2CH_3$ | —$CH_3$ | —H |
| 0 | —$CH_2CH_2$—O—$CH_3$ | —H | —$CH_2CH_3$ | —$CH_3$ | —H |
| 0 | —$CH_2CH_2$—O—$CH_2CH_3$ | —H | —$CH_2CH_3$ | —$CH_3$ | —H |

TABLE 5

| n | $R_1$ | $R_2$ | $R_3$ | $R_4$ | $R_5$ |
|---|---|---|---|---|---|
| 0 | —$CH_2$—O—$CH_3$ | —$CH_3$ | —$CH_2CH_3$ | —$CH_3$ | —H |
| 0 | —$CH_2$—O—$CH_2CH_3$ | —$CH_3$ | —$CH_2CH_3$ | —$CH_3$ | —H |
| 0 | —$CH(CH_3)$—O—$CH_3$ | —$CH_3$ | —$CH_2CH_3$ | —$CH_3$ | —H |
| 0 | —$CH(CH_3)$—O—$CH_2CH_3$ | —$CH_3$ | —$CH_2CH_3$ | —$CH_3$ | —H |
| 0 | —$CH_2CH_2$—O—$CH_3$ | —$CH_3$ | —$CH_2CH_3$ | —$CH_3$ | —H |
| 0 | —$CH_2CH_2$—O—$CH_2CH_3$ | —$CH_3$ | —$CH_2CH_3$ | —$CH_3$ | —H |

TABLE 6

| n | $R_1$ | $R_2$ | $R_3$ | $R_4$ | $R_5$ |
|---|---|---|---|---|---|
| 0 | —$CH_2$—O—$CH_3$ | —$CH_2CH_3$ | —$CH_2CH_3$ | —$CH_3$ | —H |
| 0 | —$CH_2$—O—$CH_2CH_3$ | —$CH_2CH_3$ | —$CH_2CH_3$ | —$CH_3$ | —H |
| 0 | —$CH(CH_3)$—O—$CH_3$ | —$CH_2CH_3$ | —$CH_2CH_3$ | —$CH_3$ | —H |
| 0 | —$CH(CH_3)$—O—$CH_2CH_3$ | —$CH_2CH_3$ | —$CH_2CH_3$ | —$CH_3$ | —H |

TABLE 6-continued

| n | $R_1$ | $R_2$ | $R_3$ | $R_4$ | $R_5$ |
|---|---|---|---|---|---|
| 0 | —CH$_2$CH$_2$—O—CH$_3$ | —CH$_2$CH$_3$ | —CH$_2$CH$_3$ | —CH$_3$ | —H |
| 0 | —CH$_2$CH$_2$—O—CH$_2$CH$_3$ | —CH$_2$CH$_3$ | —CH$_2$CH$_3$ | —CH$_3$ | —H |

TABLE 7

| n | $R_1$ | $R_2$ | $R_3$ | $R_4$ | $R_5$ |
|---|---|---|---|---|---|
| 0 | —CH$_2$—O—CH$_3$ | —H | —CH$_3$ | —CH$_3$ | —CH$_3$ |
| 0 | —CH$_2$—O—CH$_2$CH$_3$ | —H | —CH$_3$ | —CH$_3$ | —CH$_3$ |
| 0 | —CH(CH$_3$)—O—CH$_3$ | —H | —CH$_3$ | —CH$_3$ | —CH$_3$ |
| 0 | —CH(CH$_3$)—O—CH$_2$CH$_3$ | —H | —CH$_3$ | —CH$_3$ | —CH$_3$ |
| 0 | —CH$_2$CH$_2$—O—CH$_3$ | —H | —CH$_3$ | —CH$_3$ | —CH$_3$ |
| 0 | —CH$_2$CH$_2$—O—CH$_2$CH$_3$ | —H | —CH$_3$ | —CH$_3$ | —CH$_3$ |

TABLE 8

| n | $R_1$ | $R_2$ | $R_3$ | $R_4$ | $R_5$ |
|---|---|---|---|---|---|
| 0 | —CH$_2$—O—CH$_3$ | —CH$_3$ | —CH$_3$ | —CH$_3$ | —CH$_3$ |
| 0 | —CH$_2$—O—CH$_2$CH$_3$ | —CH$_3$ | —CH$_3$ | —CH$_3$ | —CH$_3$ |
| 0 | —CH(CH$_3$)—O—CH$_3$ | —CH$_3$ | —CH$_3$ | —CH$_3$ | —CH$_3$ |
| 0 | —CH(CH$_3$)—O—CH$_2$CH$_3$ | —CH$_3$ | —CH$_3$ | —CH$_3$ | —CH$_3$ |
| 0 | —CH$_2$CH$_2$—O—CH$_3$ | —CH$_3$ | —CH$_3$ | —CH$_3$ | —CH$_3$ |
| 0 | —CH$_2$CH$_2$—O—CH$_2$CH$_3$ | —CH$_3$ | —CH$_3$ | —CH$_3$ | —CH$_3$ |

TABLE 9

| n | $R_1$ | $R_2$ | $R_3$ | $R_4$ | $R_5$ |
|---|---|---|---|---|---|
| 0 | —CH$_2$—O—CH$_3$ | —CH$_2$CH$_3$ | —CH$_3$ | —CH$_3$ | —CH$_3$ |
| 0 | —CH$_2$—O—CH$_2$CH$_3$ | —CH$_2$CH$_3$ | —CH$_3$ | —CH$_3$ | —CH$_3$ |
| 0 | —CH(CH$_3$)—O—CH$_3$ | —CH$_2$CH$_3$ | —CH$_3$ | —CH$_3$ | —CH$_3$ |
| 0 | —CH(CH$_3$)—O—CH$_2$CH$_3$ | —CH$_2$CH$_3$ | —CH$_3$ | —CH$_3$ | —CH$_3$ |
| 0 | —CH$_2$CH$_2$—O—CH$_3$ | —CH$_2$CH$_3$ | —CH$_3$ | —CH$_3$ | —CH$_3$ |
| 0 | —CH$_2$CH$_2$—O—CH$_2$CH$_3$ | —CH$_2$CH$_3$ | —CH$_3$ | —CH$_3$ | —CH$_3$ |

TABLE 10

| n | $R_1$ | $R_2$ | $R_3$ | $R_4$ | $R_5$ |
|---|---|---|---|---|---|
| 0 | —CH$_2$—O—CH$_3$ | —H | —CH$_3$ | —CH$_3$ | —OH |
| 0 | —CH$_2$—O—CH$_2$CH$_3$ | —H | —CH$_3$ | —CH$_3$ | —OH |
| 0 | —CH(CH$_3$)—O—CH$_3$ | —H | —CH$_3$ | —CH$_3$ | —OH |
| 0 | —CH(CH$_3$)—O—CH$_2$CH$_3$ | —H | —CH$_3$ | —CH$_3$ | —OH |
| 0 | —CH$_2$CH$_2$—O—CH$_3$ | —H | —CH$_3$ | —CH$_3$ | —OH |
| 0 | —CH$_2$CH$_2$—O—CH$_2$CH$_3$ | —H | —CH$_3$ | —CH$_3$ | —OH |

TABLE 11

| n | $R_1$ | $R_2$ | $R_3$ | $R_4$ | $R_5$ |
|---|---|---|---|---|---|
| 0 | —CH$_2$—O—CH$_3$ | —CH$_3$ | —CH$_3$ | —CH$_3$ | —OH |
| 0 | —CH$_2$—O—CH$_2$CH$_3$ | —CH$_3$ | —CH$_3$ | —CH$_3$ | —OH |
| 0 | —CH(CH$_3$)—O—CH$_3$ | —CH$_3$ | —CH$_3$ | —CH$_3$ | —OH |
| 0 | —CH(CH$_3$)—O—CH$_2$CH$_3$ | —CH$_3$ | —CH$_3$ | —CH$_3$ | —OH |
| 0 | —CH$_2$CH$_2$—O—CH$_3$ | —CH$_3$ | —CH$_3$ | —CH$_3$ | —OH |
| 0 | —CH$_2$CH$_2$—O—CH$_2$CH$_3$ | —CH$_3$ | —CH$_3$ | —CH$_3$ | —OH |

TABLE 12

| n | $R_1$ | $R_2$ | $R_3$ | $R_4$ | $R_5$ |
|---|---|---|---|---|---|
| 0 | —CH$_2$—O—CH$_3$ | —CH$_2$CH$_3$ | —CH$_3$ | —CH$_3$ | —OH |
| 0 | —CH$_2$—O—CH$_2$CH$_3$ | —CH$_2$CH$_3$ | —CH$_3$ | —CH$_3$ | —OH |

TABLE 12-continued

| n | $R_1$ | $R_2$ | $R_3$ | $R_4$ | $R_5$ |
|---|---|---|---|---|---|
| 0 | —CH(CH$_3$)—O—CH$_3$ | —CH$_2$CH$_3$ | —CH$_3$ | —CH$_3$ | —OH |
| 0 | —CH(CH$_3$)—O—CH$_2$CH$_3$ | —CH$_2$CH$_3$ | —CH$_3$ | —CH$_3$ | —OH |
| 0 | —CH$_2$CH$_2$—O—CH$_3$ | —CH$_2$CH$_3$ | —CH$_3$ | —CH$_3$ | —OH |
| 0 | —CH$_2$CH$_2$—O—CH$_2$CH$_3$ | —CH$_2$CH$_3$ | —CH$_3$ | —CH$_3$ | —OH |

TABLE 13

| N | $R_1$ | $R_2$ | $R_3$ | $R_4$ | $R_5$ |
|---|---|---|---|---|---|
| 0 | —CH$_2$—O—CH$_3$ | —H | —CH$_2$CH$_3$ | —CH$_2$CH$_3$ | —OH |
| 0 | —CH$_2$—O—CH$_2$CH$_3$ | —H | —CH$_2$CH$_3$ | —CH$_2$CH$_3$ | —OH |
| 0 | —CH(CH$_3$)—O—CH$_3$ | —H | —CH$_2$CH$_3$ | —CH$_2$CH$_3$ | —OH |
| 0 | —CH(CH$_3$)—O—CH$_2$CH$_3$ | —H | —CH$_2$CH$_3$ | —CH$_2$CH$_3$ | —OH |
| 0 | —CH$_2$CH$_2$—O—CH$_3$ | —H | —CH$_2$CH$_3$ | —CH$_2$CH$_3$ | —OH |
| 0 | —CH$_2$CH$_2$—O—CH$_2$CH$_3$ | —H | —CH$_2$CH$_3$ | —CH$_2$CH$_3$ | —OH |

TABLE 14

| n | $R_1$ | $R_2$ | $R_3$ | $R_4$ | $R_5$ |
|---|---|---|---|---|---|
| 0 | —CH$_2$—CO—CH$_3$ | —CH$_3$ | —CH$_2$CH$_3$ | —CH$_2$CH$_3$ | —OH |
| 0 | —CH$_2$—O—CH$_2$CH$_3$ | —CH$_3$ | —CH$_2$CH$_3$ | —CH$_2$CH$_3$ | —OH |
| 0 | —CH(CH$_3$)—O—CH$_3$ | —CH$_3$ | —CH$_2$CH$_3$ | —CH$_2$CH$_3$ | —OH |
| 0 | —CH(CH$_3$)—O—CH$_2$CH$_3$ | —CH$_3$ | —CH$_2$CH$_3$ | —CH$_2$CH$_3$ | —OH |
| 0 | —CH$_2$CH$_2$—O—CH$_3$ | —CH$_3$ | —CH$_2$CH$_3$ | —CH$_2$CH$_3$ | —OH |
| 0 | —CH$_2$CH$_2$—O—CH$_2$CH$_3$ | —CH$_3$ | —CH$_2$CH$_3$ | —CH$_2$CH$_3$ | —OH |

TABLE 15

| n | $R_1$ | $R_2$ | $R_3$ | $R_4$ | $R_5$ |
|---|---|---|---|---|---|
| 0 | —CH$_2$—O—CH$_3$ | —CH$_2$CH$_3$ | —CH$_2$CH$_3$ | —CH$_2$CH$_3$ | —OH |
| 0 | —CH$_2$—O—CH$_2$CH$_3$ | —CH$_2$CH$_3$ | —CH$_2$CH$_3$ | —CH$_2$CH$_3$ | —OH |
| 0 | —CH(CH$_3$)—O—CH$_3$ | —CH$_2$CH$_3$ | —CH$_2$CH$_3$ | —CH$_2$CH$_3$ | —OH |
| 0 | —CH(CH$_3$)—O—CH$_2$CH$_3$ | —CH$_2$CH$_3$ | —CH$_2$CH$_3$ | —CH$_2$CH$_3$ | —OH |
| 0 | —CH$_2$CH$_2$—O—CH$_3$ | —CH$_2$CH$_3$ | —CH$_2$CH$_3$ | —CH$_2$CH$_3$ | —OH |
| 0 | —CH$_2$CH$_2$—O—CH$_2$CH$_3$ | —CH$_2$CH$_3$ | —CH$_2$CH$_3$ | —CH$_2$CH$_3$ | —OH |

TABLE 16

| n | $R_1$ | $R_2$ | $R_3$—$R_4$ | $R_5$ |
|---|---|---|---|---|
| 0 | —CH$_2$—O—CH$_3$ | —H | —CH$_2$CH$_2$CH$_2$CH$_2$— | —H |
| 0 | —CH$_2$—O—CH$_2$CH$_3$ | —H | —CH$_2$CH$_2$CH$_2$CH$_2$— | —H |
| 0 | —CH(CH$_3$)—O—CH$_3$ | —H | —CH$_2$CH$_2$CH$_2$CH$_2$— | —H |
| 0 | —CH(CH$_3$)—O—CH$_2$CH$_3$ | —H | —CH$_2$CH$_2$CH$_2$CH$_2$— | —H |
| 0 | —CH$_2$CH$_2$—O—CH$_3$ | —H | —CH$_2$CH$_2$CH$_2$CH$_2$— | —H |
| 0 | —CH$_2$CH$_2$—O—CH$_2$CH$_3$ | —H | —CH$_2$CH$_2$CH$_2$CH$_2$— | —H |

TABLE 17

| n | $R_1$ | $R_2$ | $R_3$—$R_4$ | $R_5$ |
|---|---|---|---|---|
| 0 | —CH$_2$—O—CH$_3$ | —CH$_3$ | —CH$_2$CH$_2$CH$_2$CH$_2$— | —H |
| 0 | —CH$_2$—O—CH$_2$CH$_3$ | —CH$_3$ | —CH$_2$CH$_2$CH$_2$CH$_2$— | —H |
| 0 | —CH(CH$_3$)—O—CH$_3$ | —CH$_3$ | —CH$_2$CH$_2$CH$_2$CH$_2$— | —H |
| 0 | —CH(CH$_3$)—O—CH$_2$CH$_3$ | —CH$_3$ | —CH$_2$CH$_2$CH$_2$CH$_2$— | —H |
| 0 | —CH$_2$CH$_2$—O—CH$_3$ | —CH$_3$ | —CH$_2$CH$_2$CH$_2$CH$_2$— | —H |
| 0 | —CH$_2$CH$_2$—O—CH$_2$CH$_3$ | —CH$_3$ | —CH$_2$CH$_2$CH$_2$CH$_2$— | —H |

TABLE 18

| n | $R_1$ | $R_2$ | $R_3-R_4$ | $R_5$ |
|---|---|---|---|---|
| 0 | —$CH_2$—O—$CH_3$ | —$CH_2CH_3$ | —$CH_2CH_2CH_2CH_2$— | —H |
| 0 | —$CH_2$—O—$CH_2CH_3$ | —$CH_2CH_3$ | —$CH_2CH_2CH_2CH_2$— | —H |
| 0 | —$CH(CH_3)$—O—$CH_3$ | —$CH_2CH_3$ | —$CH_2CH_2CH_2CH_2$— | —H |
| 0 | —$CH(CH_3)$—O—$CH_2CH_3$ | —$CH_2CH_3$ | —$CH_2CH_2CH_2CH_2$— | —H |
| 0 | —$CH_2CH_2$—O—$CH_3$ | —$CH_2CH_3$ | —$CH_2CH_2CH_2CH_2$— | —H |
| 0 | —$CH_2CH_2$—O—$CH_2CH_3$ | —$CH_2CH_3$ | —$CH_2CH_2CH_2CH_2$— | —H |

TABLE 19

| n | $R_1$ | $R_2$ | $R_3-R_4$ | $R_5$ |
|---|---|---|---|---|
| 0 | —$CH_2$—O—$CH_3$ | —H | —$CH_2CH_2CH_2CH_2$— | —OH |
| 0 | —$CH_2$—O—$CH_2CH_3$ | —H | —$CH_2CH_2CH_2CH_2$— | —OH |
| 0 | —$CH(CH_3)$—O—$CH_3$ | —H | —$CH_2CH_2CH_2CH_2$— | —OH |
| 0 | —$CH(CH_3)$—O—$CH_2CH_3$ | —H | —$CH_2CH_2CH_2CH_2$— | —OH |
| 0 | —$CH_2CH_2$—O—$CH_3$ | —H | —$CH_2CH_2CH_2CH_2$— | —OH |
| 0 | —$CH_2CH_2$—O—$CH_2CH_3$ | —H | —$CH_2CH_2CH_2CH_2$— | —OH |

TABLE 20

| n | $R_1$ | $R_2$ | $R_3-R_4$ | $R_5$ |
|---|---|---|---|---|
| 0 | —$CH_2$—O—$CH_3$ | —$CH_3$ | —$CH_2CH_2CH_2CH_2$— | —OH |
| 0 | —$CH_2$—O—$CH_2CH_3$ | —$CH_3$ | —$CH_2CH_2CH_2CH_2$— | —OH |
| 0 | —$CH(CH_3)$—O—$CH_3$ | —$CH_3$ | —$CH_2CH_2CH_2CH_2$— | —OH |
| 0 | —$CH(CH_3)$—O—$CH_2CH_3$ | —$CH_3$ | —$CH_2CH_2CH_2CH_2$— | —OH |
| 0 | —$CH_2CH_2$—O—$CH_3$ | —$CH_3$ | —$CH_2CH_2CH_2CH_2$— | —OH |
| 0 | —$CH_2CH_2$—O—$CH_2CH_3$ | —$CH_3$ | —$CH_2CH_2CH_2CH_2$— | —OH |

TABLE 21

| n | $R_1$ | $R_2$ | $R_3-R_4$ | $R_5$ |
|---|---|---|---|---|
| 0 | —$CH_2$—O—$CH_3$ | —$CH_2CH_3$ | —$CH_2CH_2CH_2CH_2$— | —OH |
| 0 | —$CH_2$—O—$CH_2CH_3$ | —$CH_2CH_3$ | —$CH_2CH_2CH_2CH_2$— | —OH |
| 0 | —$CH(CH_3)$—O—$CH_3$ | —$CH_2CH_3$ | —$CH_2CH_2CH_2CH_2$— | —OH |
| 0 | —$CH(CH_3)$—O—$CH_2CH_3$ | —$CH_2CH_3$ | —$CH_2CH_2CH_2CH_2$— | —OH |
| 0 | —$CH_2CH_2$—O—$CH_3$ | —$CH_2CH_3$ | —$CH_2CH_2CH_2CH_2$— | —OH |
| 0 | —$CH_2CH_2$—O—$CH_2CH_3$ | —$CH_2CH_3$ | —$CH_2CH_2CH_2CH_2$— | —OH |

The disclosure provides a method of inducing cytokine biosynthesis in a human or animal by administering to the human or animal an effective amount of a compound or salt selected from the group consisting of any one of the above embodiments of Formula (I), which may be embodiments of Formula (II) and/or Formula (III).

The disclosure provides a method of inducing IFN-alpha biosynthesis in a human or animal by administering to the human or animal an effective amount of a compound or salt selected from any one of the above embodiments of Formula (I), which may be embodiments of Formula (II) and/or Formula (III).

The disclosure provides a method of inducing IFN-gamma biosynthesis in a human or animal by administering to the human or animal an effective amount of a compound or salt selected from any one of the above embodiments of Formula (I), which may be embodiments of Formula (II) and/or Formula (III).

The disclosure provides a method of inducing TNF-alpha biosynthesis in a human or animal by administering to the human or animal an effective amount of a compound or salt selected from any one of the above embodiments of Formula (I), which may be embodiments of Formula (II) and/or Formula (III).

The disclosure provides a method for treating a viral disease in a human or animal by administering to the human or animal an effective amount of a compound or salt selected from any one of the above embodiments of Formula (I), which may be embodiments of Formula (II) and/or Formula (III).

The disclosure provides a method for treating a neoplastic disease in a human or animal by administering to the human or animal an effective amount of a compound or salt selected from any one of the above embodiments of Formula (I), which may be embodiments of Formula (II) and/or Formula (III).

The compounds, and salts thereof, of the disclosure may be synthesized by synthetic routes that include processes analogous to those well known in the chemical arts, particularly in light of the description contained herein. The starting materials are generally available from commercial sources such as the Sigma-Aldrich Company (St. Louis, MO) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Compounds of the disclosure can be prepared, for example, according to Reaction Schemes I, II, and III where R, $R_2$, $R_3$, $R_4$, $R_5$, X, Y and n are as described above. In step (1) of Reaction Scheme I, an amino substituted carboxylic acid of Formula IV can be reacted with iodine and sodium borohydride in an ether solvent to provide the alcohol substituted compound of Formula V. The designator 'm' can be 0, 1, or 2. When m=0, the compound of Formula IV is an alpha-amino carboxylic acid (for example valine or tert-leucine). When m=1, the resulting alkyl linking group can be unsubstituted or substituted with a methyl group. In some cases, compounds of Formula V are commercially available (for example valinol) eliminating the need for step (1). In step (2), the primary amine of Formula V can be reacted with di-tert-butyl-dicarbonate [$Boc_2O$] and triethylamine to provide the Boc protected amine compound of Formula VI.

The alcohol group of the compound of Formula VI can be reacted in step (3) with sodium hydroxide and a dialkyl sulfate (such as for example dimethyl sulfate or diethyl sulfate) to provide the alkyl ether of Formula VII. Alternatively, the alcohol group of the compound of Formula VI can be reacted in step (3) with a base (for example sodium hydride) and an alkyl halide to provide the alkyl ether of Formula VII (Liu, Y., et al., *Organic Process Research & Development*, 2014, 18, pages 1142-1144). The Boc amino protecting group in the compound of Formula VII can be removed in step (4) by reacting the compound of Formula VII with hydrochloric acid in an alcohol solvent (for example methanol or ethanol) to provide the primary amine compound of Formula VIII. It is often convenient to isolate the compound of Formula VIII as a hydrochloride salt.

Reaction Scheme I

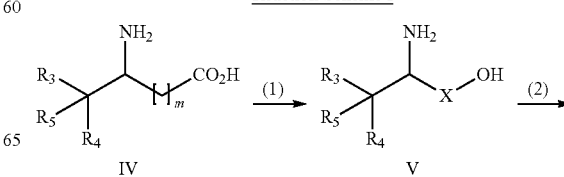

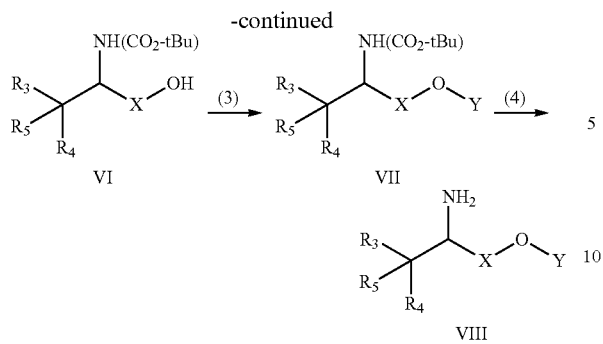

In Reaction Scheme II, a 4-chloro-3-nitroquinoline of Formula IX is reacted in step (5) with the compound of Formula VIII to provide a 3-nitroquinolin-4-amine of Formula X. The reaction can be carried out by adding the amine of Formula VIII to a solution of Formula IX in a suitable solvent such as dichloromethane in the presence of a tertiary amine such as triethylamine. The 4-chloro-3-nitroquinoline compound of Formula IX and substituted analogs are known compounds (see, for example, U.S. Pat. No. 3,700,674 (Diehl et al.), U.S. Pat. No. 5,389,640 (Gerster et al.), U.S. Pat. No. 6,110,929 (Gerster et al.), U.S. Pat. No. 7,923,560 (Wightman et al.), and references cited therein). In many cases, substituted analogs of Formula IX (for example n=1 and R being a halogen, alkoxy or benzyloxy group) can be prepared starting with commercially available substituted anilines.

In step (6) of Reaction Scheme II, the nitro group of Formula X can be reduced to an amino group. The reduction can be carried out in a pressure bottle using hydrogen, a catalytic amount of palladium or platinum on carbon, and a solvent such as methanol, acetonitrile, toluene, or combinations thereof. The reaction can be carried out with a Parr apparatus. Alternatively, the desired reduction can be accomplished using sodium dithionite and catalytic dioctyl viologen in a two phase dichloromethane-water solvent system. In step (7) of Reaction Scheme II, the resulting 3,4-diamine compound can be reacted with a carboxylic acid ($R_2CO_2H$) to provide a 1H-imidazo[4,5-c]quinoline of Formula XI. Suitable equivalents to carboxylic acids such as acyl chlorides, thioesters, and 1,1-dialkoxyalkyl alkanoates can also be used. The carboxylic acid or equivalent is selected so that it will provide the desired $R_2$ substituent in a compound of Formula XI. For example, triethylorthoformate will provide a compound where $R_2$ is hydrogen and trimethyl orthovalerate will provide a compound where $R_2$ is n-butyl. The reaction can be carried out without a solvent or with an inert solvent (for example ethyl acetate or n-propyl acetate). Optionally, a catalyst such as pyridine hydrochloride can be included.

In step (8) of Reaction Scheme II, the 1H-imidazo[4,5-c]quinoline of Formula XI can be oxidized to provide a 1H-imidazo[4,5-c]quinoline-5N-oxide using a conventional oxidizing agent capable of forming an N-oxide. Preferably, a solution of the compound of Formula XI in a suitable solvent such as chloroform or dichloromethane is reacted with 3-chloroperbenzoic acid (MCPBA) at ambient temperature.

In step (9) of Reaction Scheme II, the N-oxide compound can be aminated to provide a 1H-imidazo[4,5-c]quinoline-4-amine of Formula XII. Step (9) involves reacting the N-oxide compound with an acylating agent and an animating agent in an inert solvent such as dichloromethane or chloroform. Suitable acylating agents include alkyl- or arylsulfonyl chlorides such as benzenesulfonyl chloride, methanesulfonyl chloride, or para-toluenesulfonyl chloride. Ammonium hydroxide is a suitable animating agent. The compound of Formula XII can optionally be isolated as an organic or inorganic salt (for example as an HCl salt). Formula XII is an embodiment of Formula I.

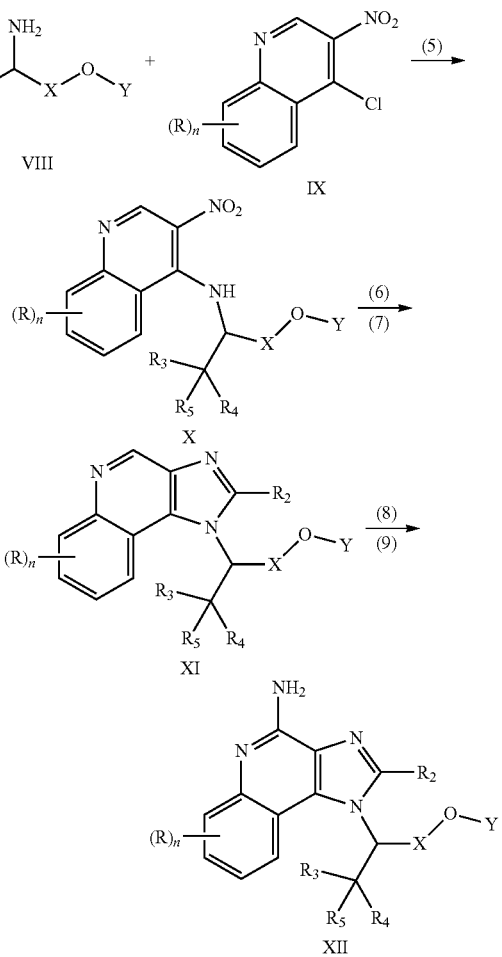

Reaction Scheme II

In step (10) of Reaction Scheme III, a Grignard reaction can be used to convert the methyl ester substituent of the oxazoline ring of Formula XIII to the tertiary alcohol of Formula XIV. Examples of suitable Grignard reagents include methyl magnesium bromide, ethyl magnesium bromide, n-propyl magnesium chloride and the like. Compounds of Formulas XIII and XIV can be prepared according to the procedures described by Williams, L., et al., *Tetrahedron*, 1996, 52(36), pages 11673-11694. The substituent $R_5$ can be either a hydrogen, a methyl group, or an ethyl group. In embodiments where $R_3$ and $R_4$ are combined to form a ring, then the methyl ester group of the compound of Formula XIII can be reacted in step (10) with an alkyl(bis magnesium bromide) to provide a cycloalkanol of Formula XIV (Grignard reaction). Alternatively, the compound of Formula XIII can be reacted in step (10) with at least 2 equivalents of a Grignard reagent that contains a vinyl substituted alkyl group (such as for example allyl magnesium bromide and 3-butenylmagnesium bromide) to convert the carboxylic acid ester group to a tertiary alcohol. A subsequent Grubb's ring-closing olefin metathesis reaction step can be used to provide the compound of Formula XIV as a cycloalkenol. The double bond in the ring can be reduced using hydrogenation conditions (hydrogen with palladium on carbon and a solvent such as methanol) to provide a saturated cycloalkanol ring.

Treatment of the compound of Formula XIV in step (11) with dilute hydrochloric acid (about 1N) in an ether solvent (such as tetrahydrofuran) can provide the compound of Formula XV. The compound of Formula XV can be reacted in step (12) with sodium hydroxide and a dialkyl sulfate (such as for example dimethyl sulfate or diethyl sulfate) to provide the alkyl ether of Formula XVI. Alternatively, the compound of Formula XV can be reacted in step (12) with a base (for example sodium hydride) and an alkyl halide to provide the alkyl ether of Formula XVI. The Boc amino protecting group in the compound of Formula XVI can be removed in step (13) by reacting the compound of Formula XVI with hydrochloric acid in an alcohol solvent (for example methanol or ethanol) to provide the primary amine compound of Formula XVII. It is often convenient to isolate the compound of Formula XVII as a hydrochloride salt. The compound of Formula XVII can be further reacted according to steps (5-9) described in Reaction Scheme II to provide compounds of Formula XII where $R_5$ is —OH.

Reaction Scheme III

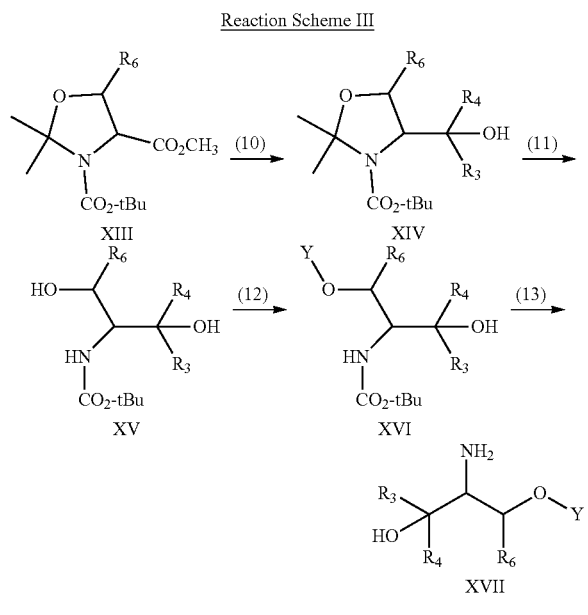

For Reaction Schemes I-III, the compounds are drawn as racemic. It is understood that these reaction schemes can also be followed starting with compounds of high enantiomeric purity (for example a D or L amino acid) to prepare final compounds of the disclosure in high enantiomeric purity.

Alternatively, a racemic mixture of reactants or reactants of low enantiomeric purity (for example 10-70% enantiomeric excess) can be used with the final product isolated as the desired Formula (II) enantiomer using any suitable procedure for the resolution of a mixture of enantiomers. A well-known method for the resolution of a mixture of enantiomers is HPLC using a column with a chiral stationary phase (CSP). Another standard method for the resolution of a mixture of enantiomers involves reacting the mixture with an optically pure carboxylic acid to form diastereomeric salts that can be readily separated by for example recrystallization or chromatography methods. Regeneration of the free base completes the resolution process. Examples of resolving agents that are available in high enantiomeric purity include, but are not limited to, (+)-tartaric acid, (−)-mandelic acid, (−)-malic acid, (+)-camphor-10-sulfonic acid, and (+)-2,3-dibenzoyltartaric acid. If needed, different types of resolution steps can be combined and multiple resolution steps can be utilized to achieve the desired enantiomeric purity. The enantiomeric purity is represented as the percent enantiomeric excess (% ee). Methods for the resolution of isomers are described in the references: Y. Okamoto, Chemical Society Reviews, 2008, 37, pages 2593-2608; G. Gubitz, Biopharmaceutics and Drug Disposition, 2001, 22, pages 291-336; and S. Mane, Analytical Methods, 2016, 8, pages 7567-7586.

In the preparation of the compounds, or salts thereof, of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in P. G. M. Wuts, Greene's Protective Groups in Organic Synthesis, John Wiley & Sons, New York, USA, 2014.

Conventional methods and techniques of separation and purification can be used to isolate the IRM compounds used in the compositions of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

The enantiomeric excess of the compounds, or salts thereof, of the disclosure can be determined using standard analytical assays such as gas chromatography or HPLC with a column having a chiral stationary phase (CSP). Suitable columns with a CSP are available from Chiral Technologies, Inc., Westchester, PA.

Enantiomeric excess (% ee) is calculated according to Equation 1.

$$\text{enantiomeric excess (\% } ee) = \frac{\left(\begin{array}{c}\text{mole \% of}\\ \text{major enantiomer}\end{array}\right) - \left(\begin{array}{c}\text{mol \% of}\\ \text{minor enantiomer}\end{array}\right)}{\left(\begin{array}{c}\text{mole \% of}\\ \text{major enantiomer}\end{array}\right) + \left(\begin{array}{c}\text{mole \% of}\\ \text{minor enantiomer}\end{array}\right)} \times 100. \quad \text{Equation 1}$$

Enantiomeric excess (% ee) can be calculated from a chiral HPLC chromatogram by comparing the peak areas of the major enantiomer and minor enantiomer signals according to Equation 2.

$$\text{enantiomeric excess (\% } ee) = \frac{\left(\begin{array}{c}\text{peak area of}\\ \text{major enantiomer}\end{array}\right) - \left(\begin{array}{c}\text{peak area of}\\ \text{minor enantiomer}\end{array}\right)}{\left(\begin{array}{c}\text{peak area of}\\ \text{major enantiomer}\end{array}\right) + \left(\begin{array}{c}\text{peak area of}\\ \text{minor enantiomer}\end{array}\right)} \times 100. \quad \text{Equation 2}$$

Prodrugs of the disclosed compounds can also be prepared by attaching to the compounds a functional group that can be cleaved under physiological conditions. Typically, a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella. "Prodrugs as Novel Delivery Systems", vol. 14 of the ACS Symposium Series, and in Bioreversible Carriers in Drug Design, ed. Edward B. Roche, American Pharmaceutical Association and Pergamon Press, 1987.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The compounds of Formula (I), which may be compounds of Formula (II) and/or Formula (III), or salts thereof, may be provided in any pharmaceutical composition suitable for administration to a subject (human or animal) and may be present in the pharmaceutical composition in any suitable form (for example as a solution, a suspension, an emulsion, or any form of a mixture). The pharmaceutical composition may be formulated with any pharmaceutically acceptable excipient, carrier, or vehicle. In some embodiments, the pharmaceutically acceptable carrier comprises water (for example phosphate buffered saline or citrate buffered saline). In some embodiments, the pharmaceutically acceptable carrier comprises an oil (for example corn, sesame, cottonseed, soybean, or safflower oil). The pharmaceutical composition may further include one or more additives including suspending agents, surfactants, dispersing agents, and preservatives (such as an anti-oxidant).

In some embodiments of the pharmaceutical composition, the compounds of Formula (I), which may be compounds of Formula (II) and/or Formula (III), or salts thereof, can be incorporated in a homogeneously dispersed formulation. In some embodiments of the pharmaceutical composition, the compounds of Formula (I), which may be compounds of Formula (II) and/or Formula (III), or salts thereof, can be incorporated in an emulsified formulation. In some embodiments of the pharmaceutical composition, the compounds of Formula (I), which may be compounds of Formula (II) and/or Formula (III), or salts thereof, can be incorporated in an oil-in-water formulation. An oil-in-water formulation can comprise an oil component, an aqueous component, and one or more surfactants (for example, formulations comprising soybean oil, TWEEN 80, SPAN 85, and phosphate buffered saline). In some embodiments of the pharmaceutical composition, the compounds of Formula (I), which may be compounds of Formula (II) and/or Formula (III), or salts thereof, can be incorporated into a liposome formulation.

In some embodiments, the pharmaceutical composition can further comprise an antigen in an amount effective to generate an immune response against the antigen. In some embodiments, the antigen is a vaccine.

The pharmaceutical composition can be administered in any suitable manner (parenterally or non-parenterally). In some embodiments, the pharmaceutical composition can be administered by an intradermal, subcutaneous, intramuscular, or intravenous injection.

In any embodiment of a pharmaceutical composition comprising a compound of Formula (II), the compound of Formula (II) is present in the composition in at least 80% enantiomeric excess, relative to the compound of Formula (III), at least 90% enantiomeric excess, at least 95% enantiomeric excess, at least 96% enantiomeric excess, at least 96% enantiomeric excess, at least 97% enantiomeric excess, at least 98% enantiomeric excess, at least 99% enantiomeric excess, at least 99.5% enantiomeric, or at least 99.8% enantiomeric excess.

In any embodiment of a pharmaceutical composition comprising a compound of Formula (III), the opposite enantiomer to the compound of Formula (II), is present in the composition in less than 10%, less than 5%, less than 2.5%, less than 2%, less than 1.5%, less than 1%, less than 0.5%, less than 0.25%, or less than 0.1%.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the concentration of a compound of Formula (I), which may be a compound of Formula (II) and/or Formula (III), or salt thereof, in the pharmaceutical composition can be at least 0.0005 mg/mF, at least 0.001 mg/mF, or at least 0.05 mg/mF. In some embodiments, the concentration of a compound of Formula (I), which may be a compound of Formula (II) and/or Formula (III), or salt thereof, in the pharmaceutical composition can be up to 2.4 mg/mF, up to 0.06 mg/mF, up to 0.01 mg/mF, or up to 0.005 mg/mF.

In some embodiments, the compositions of the disclosure will contain sufficient active ingredient (i.e., compound of Formula (I) or salt thereof) or prodrug to provide a dose of at least 100 nanograms per kilogram (ng/kg), or at least 10 micrograms per kilogram (µg/kg), of the compound or salt to the subject. In some embodiments, the compositions of the disclosure will contain sufficient active ingredient (i.e., compound of Formula (I) or salt thereof) or prodrug to provide a dose of up to 50 milligrams per kilogram (mg/kg), or up to 5 mg/kg, of the compound or salt to the subject.

In some embodiments, the compositions of the disclosure will contain sufficient active ingredient (i.e., compound of Formula (I) or salt thereof) or prodrug to provide a dose of, for example, from 0.01 mg/m$^2$ to 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or prodrug in a dose outside this range. In some of these embodiments, the method includes administering sufficient compound or salt or prodrug to provide a dose of from 0.1 mg/m$^2$ to 2.0 mg/m$^2$ to the subject, for example, a dose of from 0.4 mg/m$^2$ to 1.2 mg/m$^2$.

A variety of dosage forms may be used to administer the compounds or salts of the disclosure to a human or animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with other active agents, including antivirals, antibiotics, proteins, peptides, oligonucleotides, antibodies, etc.

Compounds or salts described herein induce the production of cytokines (e.g., IFN-alpha, IFN-gamma, TNF-alpha) in experiments performed according to the tests set forth below. These results indicate that the compounds of the disclosure, or salts thereof, are useful for activating the immune response in a number of different ways, rendering them useful in the treatment of a variety of disorders. As such, the compounds of the disclosure, or salts thereof, are agonists of cytokine biosynthesis and production, particularly agonists of IFN-alpha, IFN-gamma, and TNF-alpha cytokine biosynthesis and production.

It is believed that one way in which the compounds or salts of the disclosure induce cytokine production is through the activation of Toll-like receptors (TLRs) in the immune system, particularly TLR-7 and/or TLR-8; however, other mechanisms may be involved. It is believed that in the immune system pathways (i.e., mechanisms) for cytokine induction, the compounds or salts of the disclosure, primarily act as agonists of TLR-7 and/or TLR-8, however, other pathways or activities may be involved.

Administration of the compounds or salts described herein can induce the production of interferon-alpha (IFN-alpha), interferon-gamma (IFN-gamma), and tumor necrosis factor-alpha (TNF-alpha) in cells. Cytokines whose biosynthesis can be induced by compounds or salts of the disclosure include IFN-alpha, IFN-gamma, TNF-alpha, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in a human or animal by administering an effective amount of a compound or salt of the disclosure to the human or animal. The human or animal to which the compound or salt is administered for induction of cytokine production may have one or more diseases, disorders, or conditions described below, for example, a viral disease or a neoplastic disease, and administration of the compound or salt may provide therapeutic treatment. Alternatively, the compound or salt may be administered to the human or animal prior to the human or animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

Viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenza virus, avian influenza), a paramyxovirus (e.g., parainfluenza virus, mumps virus, measles virus, and respiratory syncytial virus (RSV)), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), and ebola virus;

Neoplastic diseases such as bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such as atopic dermatitis or eczema, eosinophilia, asthma, allergy, allergic rhinitis, and Omenn's syndrome;

Diseases associated with wound repair, such as, for example, inhibition of keloid formation and other types of scarring (e.g., enhancing wound healing, including chronic wounds); and Parasitic diseases including but not limited to malaria, leishmaniasis, cryptosporidiosis, toxoplasmosis, and trypanosome infection.

In addition, a compound, salt, or pharmaceutical composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, hepatitis A vaccine, hepatitis B vaccine, hepatitis C vaccine, influenza A vaccine, influenza B vaccine, malaria vaccine, parainfluenza vaccine, polio vaccine, rabies vaccine, measles vaccine, mumps vaccine, rubella vaccine, yellow fever vaccine, tetanus vaccine, diphtheria vaccine, hemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, ebola virus vaccine.

Compounds, salts, or pharmaceutical compositions identified herein may be particularly useful as vaccine adjuvants when used in conjunction with tumor antigens associated with colorectal cancer, head and neck cancer, breast cancer, lung cancer and melanoma.

Compounds, salts, or pharmaceutical compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in a human or animal in need thereof (having the disease) by administering a therapeutically effective amount of a compound, salt, or composition to the human or animal.

A human or animal may also be vaccinated by administering an effective amount of a compound, salt, or composition described herein as a vaccine adjuvant. In one embodiment, a method of vaccinating a human or animal includes administering an effective amount of a compound, salt, or composition described herein to the human or animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds, salts, or compositions identified herein may be used as prophylactic or therapeutic vaccine adjuvants in veterinary applications. Compounds, salts, or compositions identified herein may be administered to, for example, pigs, horses, cattle, sheep, dogs, cats, poultry (such as chickens or turkeys), etc.

Compounds or salts or compositions identified herein may be particularly useful when an effective amount is administered to a human or animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e., applied directly to the surface of a tumor, a lesion, a wart, or an infected tissue, etc.).

In one embodiment an effective amount of compound, salt, or composition described herein, such as an aqueous composition is administered into the bladder of a human or animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, and TNF-alpha that is increased (induced) over a background level of such cytokines. The precise dose will vary according to factors known in the art but is typically to be a dose of 100 ng/kg to 50 mg/kg, or 10 µg/kg to 5 mg/kg. In other embodiments, the amount can be, for example, from 0.01 mg/m$^2$ to 5.0 mg/m$^2$ (computed according to the Dubois method as described above), although in other embodiments the induction of cytokine biosynthesis may be performed by administering a compound or salt in a dose outside this range. In some of these embodiments, the method includes administering sufficient compound or salt or composition to provide a dose from 0.1 mg/m$^2$ to 2.0 mg/m$^2$ to the subject, for example, a dose of from 0.4 mg/m$^2$ to 1.2 mg/m$^2$.

A method of treating a viral infection in a human or animal and a method of treating a neoplastic disease in a human or animal can include administering an effective amount of a compound or salt described herein to the human or animal.

An effective amount to treat or inhibit a viral infection can be an amount that will cause a reduction in one or more of the manifestations of viral infection, such as viral lesions, viral load, rate of virus production, and mortality as compared to untreated humans or animals. The precise amount that is effective for such treatment will vary according to factors known in the art but it is normally a dose of 100 ng/kg to 50 mg/kg, or 10 µg/kg to 5 mg/kg.

An amount of a compound or salt effective to treat a neoplastic condition can be an amount that causes a reduction in tumor size or in the number of tumor foci. The precise amount will vary according to factors known in the art but is typically 100 ng/kg to 50 mg/kg, or 10 µg/kg to 5 mg/kg. In other embodiments, the amount is typically, for example, from 0.01 mg/m$^2$ to 5.0 mg/m$^2$ (computed according to the Dubois method as described above), although in some embodiments the induction of cytokine biosynthesis may be performed by administering a compound or salt in a dose outside this range. In some of these embodiments, the method includes administering sufficient compound or salt or composition to provide a dose from 0.1 mg/m$^2$ to 2.0 mg/m$^2$ to the subject, for example, a dose of from 0.4 mg/m$^2$ to 1.2 mg/m$^2$.

EMBODIMENTS

Embodiment 1 is a compound of Formula (I), or salt thereof:

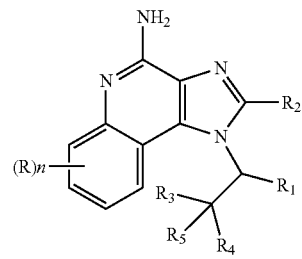

Formula (I)

wherein:
n is an integer of 0 or 1;
R is selected from the group consisting of halogen, hydroxy, alkyl, alkoxy, and —C(O)—O— alkyl;
$R_1$ is —X—O—Y where X is a $C_{1-3}$alkylene and Y is a $C_{1-3}$alkyl;
$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$;
$R_3$ is a $C_{1-4}$alkyl, $R_4$ is a $C_{1-4}$alkyl, or $R_3$ and $R_4$ are combined to form a ring of 3-7 carbon atoms optionally having one oxygen atom in the ring; and
$R_5$ is —H, —CH$_3$, —F, or —OH.

Embodiment 2 is the compound or salt of embodiment 1, which is a compound of Formula (II), or salt thereof:

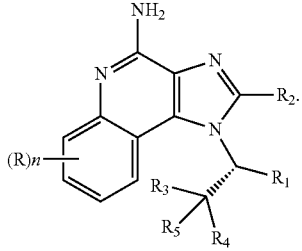

Formula (II)

Embodiment 3 is the compound or salt of embodiment 1, which is a compound of Formula (III), or salt thereof:

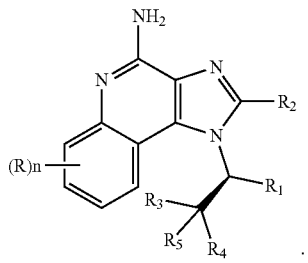

Formula (III)

Embodiment 4 is the compound or salt of any of embodiments 1 through 3, wherein R is selected from the group consisting of halogen, hydroxy, —$C_{1-12}$alkyl, —$C_{1-12}$alkoxy, and —C(O)—O—$C_{1-10}$alkyl (in some embodiments, R is selected from the group consisting of halogen, hydroxy, —$C_{1-7}$alkyl, —$C_{1-7}$alkoxy, and —C(O)—O—$C_{1-5}$alkyl).

Embodiment 5 is the compound or salt of embodiment 4, wherein R is selected from the group consisting of hydroxy, F, and Cl.

Embodiment 6 is the compound or salt of embodiment 5, wherein R is selected from the group consisting of F and Cl.

Embodiment 7 is the compound or salt of any one of embodiments 1 through 3, wherein n is 0.

Embodiment 8 is the compound or salt of any one of embodiments 1 through 7, wherein $R_1$ is —X—O—Y where X is —$CH_2$—, —$CH_2CH_2$—, or —$CH(CH_3)$—, and Y is a $C_{1-3}$alkyl.

Embodiment 9 is the compound or salt of any one of embodiments 1 through 8, wherein —$CH_2$— or —$CH(CH_3)$—, and Y is —$CH_3$ or —$CH_2CH_3$.

Embodiment 10 is the compound or salt of any one of embodiments 1 through 9, wherein $R_2$ is selected from the group consisting of hydrogen, methyl, and ethyl.

Embodiment 11 is the compound or salt of embodiment 10, wherein $R_2$ is hydrogen.

Embodiment 12 is the compound or salt of embodiment 10, wherein $R_2$ is methyl.

Embodiment 13 is the compound or salt of embodiment 10, wherein $R_2$ is ethyl.

Embodiment 14 is the compound or salt of any one of embodiments 1 through 13, wherein $R_3$ is a $C_{1-4}$alkyl.

Embodiment 15 is the compound or salt of embodiment 14, wherein $R_3$ is methyl.

Embodiment 16 is the compound or salt of embodiment 14, wherein $R_3$ is ethyl.

Embodiment 17 is the compound or salt of any one of embodiments 1 through 16, wherein $R_4$ is a $C_{1-4}$alkyl.

Embodiment 18 is the compound or salt of embodiment 17, wherein $R_4$ is methyl.

Embodiment 19 is the compound or salt of embodiment 17, wherein $R_3$ is ethyl.

Embodiment 20 is the compound or salt of embodiment 17, wherein $R_3$ and $R_4$ are each methyl.

Embodiment 21 is the compound or salt of embodiment 17, wherein $R_3$ and $R_4$ are each ethyl.

Embodiment 22 is the compound or salt of any one of embodiments 1 through 13, wherein $R_3$ and $R_4$ are combined to form a ring of 3-7 carbon atoms optionally having one oxygen atom in the ring.

Embodiment 23 is the compound or salt of embodiment 22, wherein $R_3$ and $R_4$ are combined to form a ring of 3-7 carbon atoms.

Embodiment 24 is the compound or salt of embodiment 22, wherein $R_3$ and $R_4$ are combined to form a ring of 3-7 carbon atoms having one oxygen atom in the ring.

Embodiment 25 is the compound or salt of any one of embodiments 1 through 24, wherein $R_5$ is —H.

Embodiment 26 is the compound or salt of any one of embodiments 1 through 24, wherein $R_5$ is —$CH_3$.

Embodiment 27 is the compound or salt of any one of embodiments 1 through 24, wherein $R_5$ is —OH.

Embodiment 28 is the compound or salt of any one of embodiments 1 through 3, wherein $R_1$ is —X—O—Y where X is —$CH_2$— or —$CH(CH_3)$— and Y is —$CH_3$ or —$CH_2CH_3$; $R_2$ is selected from the group consisting of hydrogen, methyl, and ethyl; $R_3$ is a $C_{1-4}$alkyl; $R_4$ is a $C_{1-4}$alkyl; $R_5$ is —H, —$CH_3$, or —OH; and n is 0.

Embodiment 29 is the compound or salt of embodiment 28, wherein $R_4$ is —X—O—Y where X is —$CH_2$— or —$CH(CH_3)$— and Y is —$CH_3$ or —$CH_2CH_3$; $R_2$ is selected from the group consisting of hydrogen, methyl, and ethyl; $R_3$ is methyl or ethyl; $R_4$ is methyl or ethyl; $R_5$ is —H, —$CH_3$, or —OH; and n is 0.

Embodiment 30 is the compound or salt of embodiment 29, wherein $R_2$ is hydrogen.

Embodiment 31 is the compound or salt of embodiment 30, wherein $R_5$ is —OH.

Embodiment 32 is the compound or salt of embodiment 31, wherein the compound is (3R)-3-(4-aminoimidazo[4,5-c]quinolin-1-yl)-4-ethoxy-2-methyl-butan-2-ol (Example 5).

Embodiment 33 is the compound or salt of embodiment 31, wherein the compound is (3 S)-3-(4-aminoimidazo[4,5-c]quinolin-1-yl)-4-ethoxy-2-methyl-butan-2-ol (Example 6).

Embodiment 34 is the compound or salt of embodiment 31, wherein the compound is (2R)-2-(4-aminoimidazo[4,5-c]quinolin-1-yl)-1-ethoxy-3-ethyl-pentan-3-ol (Example 12).

Embodiment 35 is the compound or salt of embodiment 31, wherein the compound is (3R,4S)-3-(4-aminoimidazo[4,5-c]quinolin-1-yl)-4-ethoxy-2-methyl-pentan-2-ol (Example 13).

Embodiment 36 is the compound or salt of embodiment 30, wherein $R_5$ is —$CH_3$.

Embodiment 37 is the compound or salt of embodiment 36, wherein the compound is 1-[(1S)-1-(ethoxymethyl)-2,2-dimethyl-propyl]imidazo[4,5-c]quinolin-4-amine (Example 9).

Embodiment 38 is the compound or salt of embodiment 36, wherein the compound is 1-[(1R)-1-(ethoxymethyl)-2,2-dimethyl-propyl]imidazo[4,5-c]quinolin-4-amine (Example 10).

Embodiment 39 is the compound or salt of embodiment 36, wherein the compound is 1-[(1S)-1-(methoxymethyl)-2,2-dimethyl-propyl]imidazo[4,5-c]quinolin-4-amine (Example 11).

Embodiment 40 is the compound or salt of embodiment 30, wherein $R_5$ is —H.

Embodiment 41 is the compound or salt of embodiment 40, wherein the compound is 1-[(1S)-1-(ethoxymethyl)-2-methyl-propyl]imidazo[4,5-c]quinolin-4-amine (Example 1).

Embodiment 42 is the compound or salt of embodiment 40, wherein the compound is 1-[(1R)-1-(ethoxymethyl)-2-methyl-propyl]imidazo[4,5-c]quinolin-4-amine (Example 2).

Embodiment 43 is the compound or salt of embodiment 29, wherein $R_2$ is methyl.

Embodiment 44 is the compound or salt of embodiment 43, wherein $R_5$ is —H.

Embodiment 45 is the compound or salt of embodiment 44, wherein the compound is 1-[(1S)-1-(ethoxymethyl)-2-methyl-propyl]-2-methyl-imidazo[4,5-c]quinolin-4-amine (Example 3).

Embodiment 46 is the compound or salt of embodiment 44, wherein the compound is 1-[(1R)-1-(ethoxymethyl)-2-methyl-propyl]-2-methyl-imidazo[4,5-c]quinolin-4-amine (Example 4).

Embodiment 47 is the compound or salt of embodiment 43, wherein $R_5$ is —OH.

Embodiment 48 is the compound or salt of embodiment 47, wherein the compound is (3R)-3-(4-amino-2-methyl-imidazo[4,5-c]quinolin-1-yl)-4-ethoxy-2-methyl-butan-2-ol (Example 7).

Embodiment 49 is the compound or salt of embodiment 29, wherein $R_2$ is ethyl.

Embodiment 50 is the compound or salt of embodiment 49, wherein $R_5$ is —OH.

Embodiment 51 is the compound or salt of embodiment 50, wherein the compound is (3R)-3-(4-amino-2-ethyl-imidazo[4,5-c]quinolin-1-yl)-4-ethoxy-2-methyl-butan-2-ol (Example 8).

Embodiment 52 is the compound or salt of any one of embodiments 1 through 3, wherein $R_1$ is —X—O—Y where X is —CH$_2$— or —CH(CH$_3$)— and Y is —CH$_3$ or —CH$_2$CH$_3$; $R_2$ is selected from the group consisting of hydrogen, methyl, and ethyl; $R_3$ and $R_4$ are combined to form a ring of 3-7 carbon atoms optionally having one oxygen atom in the ring; $R_5$ is —H, —CH$_3$, or —OH; and n is 0.

Embodiment 53 is the compound or salt of embodiment 52, wherein $R_2$ is hydrogen.

Embodiment 54 is the compound or salt of embodiment 53, wherein $R_5$ is —OH.

Embodiment 55 is the compound or salt of embodiment 54, wherein the compound is 1-[(1R)-1-(4-aminoimidazo[4,5-c]quinolin-1-yl)-2-ethoxy-ethyl]cyclopentanol (Example 14).

Embodiment 56 is the compound or salt of any one of embodiments 1 through 55, wherein the pharmaceutically acceptable salt is hydrochloride.

Embodiment 57 is a pharmaceutical composition comprising an effective amount of a compound or salt of any one of embodiments 1 through 56 in combination with a pharmaceutically acceptable carrier.

Embodiment 58 is the pharmaceutical composition of embodiment 57, wherein the compound of Formula (II) or salt thereof is present in at least 80%, at least 90%, at least 95%, at least 97%, or at least 98%, enantiomeric excess.

Embodiment 59 is the pharmaceutical composition of embodiment 58, wherein the compound of Formula (II) or salt thereof is present in at least 99% enantiomeric excess.

Embodiment 60 is the pharmaceutical composition of embodiment 59, wherein the compound of Formula (II) or salt thereof is present in at least 99.5% enantiomeric excess.

Embodiment 61 is the pharmaceutical composition of embodiment 60, wherein the compound of Formula (II) or salt thereof is present in at least 99.8% enantiomeric excess.

Embodiment 62 is the pharmaceutical composition of embodiment 57, wherein the compound of Formula (III) or salt thereof is present in at least 80%, at least 90%, at least 95%, at least 97%, or at least 98%, enantiomeric excess.

Embodiment 63 is the pharmaceutical composition of embodiment 62, wherein the compound of Formula (III) or salt thereof is present in at least 99% enantiomeric excess.

Embodiment 64 is the pharmaceutical composition of embodiment 63, wherein the compound of Formula (III) or salt thereof is present in at least 99.5% enantiomeric excess.

Embodiment 65 is the pharmaceutical composition of embodiment 64, wherein the compound of Formula (III) or salt thereof is present in at least 99.8% enantiomeric excess.

Embodiment 66 is the pharmaceutical composition of any one of embodiments 57 through 65, further comprising an antigen.

Embodiment 67 is the pharmaceutical composition of any one of embodiments 57 through 66 for use in treating an infectious disease in a human or animal.

Embodiment 68 is the pharmaceutical composition of embodiment 67 for use in treating a viral, bacterial, fungal, or parasitic infection in a human or animal.

Embodiment 69 is the pharmaceutical composition of any one of embodiments 57 through 66 for use in treating a neoplastic disease in a human or animal.

Embodiment 70 is a method of inducing cytokine biosynthesis in a human or animal comprising administering an effective amount of a compound or salt of any one of embodiments 1 through 56 to the human or animal.

Embodiment 71 is the method of embodiment 70 comprising administering an effective amount of 1-[(1S)-1-(ethoxymethyl)-2-methyl-propyl]imidazo[4,5-c]quinolin-4-amine (Example 1).

Embodiment 72 is the method of embodiment 70 comprising administering an effective amount of 1-[(1R)-1-(ethoxymethyl)-2-methyl-propyl]imidazo[4,5-c]quinolin-4-amine (Example 2).

Embodiment 73 is the method of embodiment 70 comprising administering an effective amount of 1-[(1S)-1-(ethoxymethyl)-2-methyl-propyl]-2-methyl-imidazo[4,5-c]quinolin-4-amine (Example 3).

Embodiment 74 is the method of embodiment 70 comprising administering an effective amount of 1-[(1R)-1-(ethoxymethyl)-2-methyl-propyl]-2-methyl-imidazo[4,5-c]quinolin-4-amine (Example 4).

Embodiment 75 is the method of embodiment 70 comprising administering an effective amount of (3R)-3-(4-aminoimidazo[4,5-c]quinolin-1-yl)-4-ethoxy-2-methyl-butan-2-ol (Example 5).

Embodiment 76 is the method of embodiment 70 comprising administering an effective amount of (3R)-3-(4-amino-2-methyl-imidazo[4,5-c]quinolin-1-yl)-4-ethoxy-2-methyl-butan-2-ol (Example 7).

Embodiment 77 is the method of embodiment 70 comprising administering an effective amount of (3R)-3-(4-amino-2-ethyl-imidazo[4,5-c]quinolin-1-yl)-4-ethoxy-2-methyl-butan-2-ol (Example 8).

Embodiment 78 is the method of embodiment 70 comprising administering an effective amount of 1-[(1S)-1-(ethoxymethyl)-2,2-dimethyl-propyl]imidazo[4,5-c]quinolin-4-amine (Example 9).

Embodiment 79 is the method of embodiment 70 comprising administering an effective amount of 1-[(1R)-1-(ethoxymethyl)-2,2-dimethyl-propyl]imidazo[4,5-c]quinolin-4-amine (Example 10).

Embodiment 80 is the method of embodiment 70 comprising administering an effective amount of 1-[(1S)-1-(methoxymethyl)-2,2-dimethyl-propyl]imidazo[4,5-c]quinolin-4-amine (Example 11).

Embodiment 81 is the method of embodiment 70 comprising administering an effective amount of (2R)-2-(4-aminoimidazo[4,5-c]quinolin-1-yl)-1-ethoxy-3-ethyl-pentan-3-ol (Example 12).

Embodiment 82 is the method of embodiment 70 comprising administering an effective amount of (3R,4S)-3-(4-aminoimidazo[4,5-c]quinolin-1-yl)-4-ethoxy-2-methyl-pentan-2-ol (Example 13).

Embodiment 83 is the method of embodiment 70 comprising administering an effective amount of 1-[(1R)-1-(4-aminoimidazo[4,5-c]quinolin-1-yl)-2-ethoxy-ethyl]cyclopentanol (Example 14).

Embodiment 84 is the method of any of embodiments 70 through 83, wherein the cytokine is IFN-alpha.

Embodiment 85 is the method of any of embodiments 70 through 83, wherein the cytokine is IFN-gamma.

Embodiment 86 is the method of any of embodiments 70 through 83, wherein the cytokine is TNF-alpha.

Embodiment 87 is a method of inhibiting cytokine biosynthesis in a human or animal comprising administering an effective amount of (3S)-3-(4-aminoimidazo[4,5-c]quinolin-1-yl)-4-ethoxy-2-methyl-butan-2-ol (Example 6) to the human or animal.

Embodiment 88 is a compound or salt of any one of embodiments 1 through 56 for use as a vaccine adjuvant in treating an infectious disease in a human or animal.

Embodiment 89 is a compound or salt of any one of embodiments 1 through 56 for use as a vaccine adjuvant in treating a viral, bacterial, fungal, or parasitic infection in a human or animal.

Embodiment 90 is a compound or salt of embodiment 88 or 89, wherein the treatment is a therapeutic or prophylactic treatment.

Embodiment 91 is a method of treating a neoplastic disease in a human or animal by administering an effective amount of a compound or salt of any one of embodiments 1 through 56 to the human or animal.

Embodiment 92 is the method of embodiment 91 wherein the neoplastic disease is selected from bladder cancer, cervical dysplasia, cervical cancer, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and combinations thereof.

EXAMPLES

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

Automated flash chromatography (AFC) was carried out using an ISOLARA HPFC system (an automated high-performance flash purification product available from Biotage Incorporated, Charlottesville, VA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Proton nuclear magnetic resonance ($^1$H NMR) analysis was conducted using a BRUKER A500 NMR spectrometer (Bruker Corporation, Billerica, MA).

Dimethylsulfoxide (DMSO) was obtained from VWR International, Radnor, PA.

10% Palladium on carbon, 3-chloroperbenzoic acid (57-86%, MCPBA), allyl magnesium bromide in diethyl ether (1.0 M), sodium borohydride, 3-bromopyridine, triethyl orthoacetate, thionyl chloride, and iodoethane were obtained from the Sigma-Aldrich Company, St. Louis, MO.

Triethyl orthoformate, D-threonine, 2,2-dimethoxypropane, dimethylaminopyridine, 3% platinum on carbon, n-propyl acetate, para-toluenesulfonyl chloride, diethyl sulfate, potassium tert-butoxide, methyl magnesium bromide in diethyl ether (3.0 M), ethyl magnesium bromide in diethyl ether (3.0 M), 1.0 N solution of tetrabutylammonium fluoride in tetrahydrofuran, and pyridine hydrochloride were obtained from the Alfa Aesar Company, Haverhill, MA.

L-tert-leucine, D-tert-leucine, camphor sulfonic acid, di-tert-butyl dicarbonate, tert-butyldimethylsilyl triflate (50% solution in toluene), 3-chloroperbenzoic acid (80%, MCPBA), and tetrabutylammonium chloride were obtained from Oakwood Products Incorporated, Estill, SC.

L-valinol, and D-valinol, were obtained from TCI America, Portland, OR.

Benzylidene[1,3-bis(2,4,6-trimethylphenyl)-2-imidazolidinylidene]dichloro(tricyclohexylphosphine)ruthenium [CAS Number 246047-72-3] was obtained from the Oxchem Corporation, Wood Dale, IL.

Triethylamine was obtained from EMD Millipore Corporation, Darmstadt Germany.

Triethyl orthopropionate was obtained from Avocado Research Chemicals, Heysham, Lancashire, UK.

Example 1

1-[(1S)-1-(ethoxymethyl)-2-methyl-propyl]imidazo[4,5-c]quinolin-4-amine

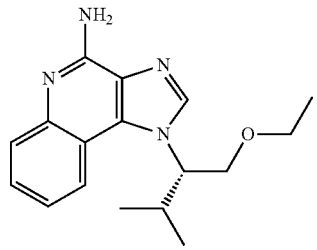 [SMILES: CCOC[C@H](C(C)C)n1cnc2c(N)nc3ccccc3c21]

Part A

To a stirred solution of L-valinol (2.06 g, 20.0 mmol) dissolved in 30 mL of dichloromethane were added di-tert-butyl dicarbonate (4.36 g, 20.0 mmol) and triethylamine (3.00 mL, 21.6 mmol) and the reaction mixture was stirred for 3 hours. The reaction mixture was then treated with 10% citric acid solution and the layers were separated. The organic portion was washed successively with 10% citric acid solution, water and brine, dried over Na₂SO₄, filtered and concentrated under reduced pressure to give 4.10 g of tert-butyl N-[(1S)-1-(hydroxymethyl)-2-methyl-propyl]carbamate as a colorless syrup.

Part B

To a stirred solution tert-butyl N-[(1S)-1-(hydroxymethyl)-2-methyl-propyl]carbamate (4.10 g, 20.2 mmol) dissolved in 25 mL of heptanes were added 2.1 g of 50% NaOH solution and diethyl sulfate (3.96 mL, 30.3 mmol). The reaction mixture was stirred rapidly followed by the addition of 100 mg of tetrabutylammonium chloride hydrate. After stirring overnight, the reaction mixture was quenched with saturated NH₄OH solution. After stirring for 2 hours, the reaction was diluted with 50 mL of heptanes and the layers were separated. The organic layer was washed successively with water (2×) and brine, dried over Na₂SO₄, filtered and concentrated under reduced pressure to give 3.86 g of tert-butyl N-[(1S)-1-(ethoxymethyl)-2-methyl-propyl]carbamate as a colorless syrup.

Part C

To a stirred solution of N-[(1S)-1-(ethoxymethyl)-2-methyl-propyl]carbamate (3.00 g, 13.0 mmol) dissolved in 15 mL of ethanol was added 2 mL of concentrated hydrochloric acid and the mixture was heated to reflux for 3 hours. The reaction mixture was then concentrated to dryness and then concentrated from toluene (2×) to give 1.51 g of (2S)-1-ethoxy-3-methyl-butan-2-amine hydrochloride as a white solid.

Part D

To a stirred suspension of (2S)-1-ethoxy-3-methyl-butan-2-amine hydrochloride (1.51 g, 9.04 mmol) in 20 mL of dichloromethane were added 4-chloro-3-nitroquinoline (1.69 g, 8.14 mmoL) and triethylamine (2.27 mL, 16.3 mmol) and the reaction mixture was stirred under an atmosphere of nitrogen overnight. The reaction mixture was concentrated to give a yellow solid. The solid was dissolved in 50 mL of ethyl acetate and washed with water (3×) and brine. The organic portion was dried over Na₂SO₄, filtered and concentrated to give an orange syrup. Purification by column chromatography (SiO₂, 12% ethyl acetate/hexanes-100% ethyl acetate) gave 2.15 g of N-[(1S)-1-(ethoxymethyl)-2-methyl-propyl]-3-nitro-quinolin-4-amine as a yellow syrup.

Part E

A solution of N-[(1S)-1-(ethoxymethyl)-2-methyl-propyl]-3-nitro-quinolin-4-amine (2.15 g, 7.10 mmol) dissolved in 50 mL of toluene was placed in a pressure bottle followed by the addition of 150 mg of 3% platinum on carbon. The bottle was then shaken under an atmosphere of hydrogen (40 PSI) for 3 hours. The reaction mixture was filtered through a pad of CELITE and the filtrate was concentrated under reduced pressure to give 1.93 g of N4-[(1S)-1-(ethoxymethyl)-2-methyl-propyl]quinoline-3,4-diamine as an orange syrup.

Part F

To a stirred solution of N4-[(1S)-1-(ethoxymethyl)-2-methyl-propyl]quinoline-3,4-diamine (1.38 g, 5.05 mmol) dissolved in 25 mL of n-propyl acetate were added triethyl orthoformate (1.26 mL, 7.58 mmol) and 100 mg of pyridine hydrochloride and the mixture was heated to 90° C., under an atmosphere of nitrogen, overnight. The cooled reaction mixture was diluted with 50 mL of ethyl acetate and washed successively with saturated sodium bicarbonate solution, water and brine. The organic portion was dried over Na₂SO₄, filtered and concentrated to give a light brown foam. Purification by column chromatography (SiO₂, 1% methanol/chloroform-10% methanol/chloroform) gave 1.35 g of 1-[(1S)-1-(ethoxymethyl)-2-methyl-propyl]imidazo[4,5-c]quinoline as an amber syrup.

Part G

To a stirred solution of 1-[(1S)-1-(ethoxymethyl)-2-methyl-propyl]imidazo[4,5-c]quinoline (1.35 g, 4.77 mmol) dissolved in 40 mL of dichloromethane was added 1.44 g of MCPBA (57-86%). After stirring for 90 minutes, para toluenesulfonyl chloride (1.09 g, 5.72 mmol) and 10 mL of concentrated NH₄OH solution were added to the reaction mixture. After stirring for 45 minutes, the reaction mixture was diluted with 25 mL of dichloromethane and washed with water (3×) and brine. The organic portion was dried over Na₂SO₄, filtered and concentrated under reduced pressure. Purification by column chromatography (SiO₂, 10% methanol/chloroform saturated with NH₄OH) gave a light brown syrup. The syrup was dissolved in 5 mL of ethanol and combined with 0.5 mL of concentrated hydrochloric acid and concentrated to dryness. Crystallization from propyl acetate/2-propanol gave 185 mg of 1-[(1S)-1-(ethoxymethyl)-2-methyl-propyl]imidazo[4,5-c]quinolin-4-amine hydrochloride as amber crystals. ¹H NMR (500 MHz, methanol-d₄) δ 8.60 (s, 1H), 8.49 (d, J=8.31 Hz, 1H), 7.82-7.86 (m, 1H), 7.74-7.79 (m, 1H), 7.60-7.67 (m, 1H), 5.11 (br t, J=6.30 Hz, 1H), 4.15 (dd, J=6.85, 10.76 Hz, 1H), 3.98 (dd, 0.7=2.93, 10.64 Hz, 1H), 3.53 (q, J=7.05 Hz, 2H), 2.51-2.62 (m, 1H), 1.21 (d, J=6.72 Hz, 3H), 1.10 (t, 0.7=6.97 Hz, 3H), 0.92 (d, J=6.72 Hz, 3H).

Example 2

1-[(1R)-1-(ethoxymethyl)-2-methyl-propyl]imidazo [4,5-c]quinolin-4-amine

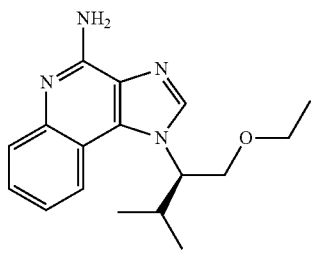 [SMILES: CCOC[C@@H](C(C)C)n1cnc2c(N)nc3ccccc3c21]

1-[(1R)-1-(ethoxymethyl)-2-methyl-propyl]imidazo[4,5-c]quinolin-4-amine was prepared from D-valinol following the procedures described in Parts A-G of Example 1 and isolated as the hydrochloride salt. ¹H NMR (500 MHz, methanol-d₄) δ 8.60 (s, 1H), 8.49 (d, J=8.31 Hz, 1H), 7.81-7.85 (m, 1H), 7.77 (dt, J=0.98, 7.76 Hz, 1H), 7.60-7.67 (m, 1H), 5.11 (br t, J=6.24 Hz, 1H), 4.14 (dd, 0.7=6.85, 10.64 Hz, 1H), 3.98 (dd, J=2.93, 10.64 Hz, 1H), 3.53 (q, J=6.97 Hz, 2H), 2.52-2.62 (m, 1H), 1.21 (d, J=6.60 Hz, 3H), 1.10 (t, J=7.03 Hz, 3H), 0.92 (d, J=6.72 Hz, 3H).

Example 3

1-[(1S)-1-(ethoxymethyl)-2-methyl-propyl]-2-methyl-imidazo[4,5-c]quinolin-4-amine

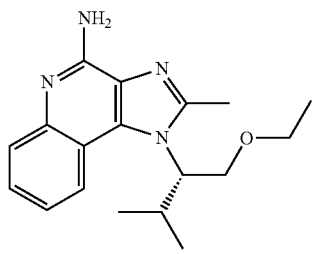 [SMILES: CCOC[C@H](C(C)C)n1c(C)nc2c(N)nc3ccccc3c21]

Part A

To a stirred solution of N4-[(1S)-1-(ethoxymethyl)-2-methyl-propyl]quinoline-3,4-diamine (510 mg, 1.87 mmol) dissolved in 25 mL of n-propyl acetate were added triethyl orthoacetate (0.51 mL, 2.80 mmol) and 100 mg of pyridine hydrochloride and the mixture was heated to 90° C., under an atmosphere of nitrogen, overnight. The cooled reaction mixture was diluted with 50 mL of ethyl acetate and washed successively with saturated sodium bicarbonate solution, water and brine. The organic portion was dried over $Na_2SO_4$, filtered and concentrated to give a light brown foam. Purification by column chromatography ($SiO_2$, 1% methanol/chloroform-10% methanol/chloroform) gave 442 mg of 1-[(1S)-1-(ethoxymethyl)-2-methyl-propyl]-2-methyl-imidazo[4,5-c]quinoline as a light brown syrup.

Part B

To a stirred solution of 1-[(1S)-1-(ethoxymethyl)-2-methyl-propyl]-2-methyl-imidazo[4,5-c]quinoline (442 mg, 1.49 mmol) dissolved in 40 mL of dichloromethane was added 500 mg of MCPBA (57-86%). After stirring for 55 minutes, para toluenesulfonyl chloride (341 mg, 1.79 mmol) and 10 mL of concentrated $NH_4OH$ solution were added to the reaction mixture. After stirring for 50 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 10% methanol/chloroform saturated with $NH_4OH$) gave a light brown syrup. Crystallization from ethyl acetate/heptanes gave 175 mg of 1-[(1S)-1-(ethoxymethyl)-2-methyl-propyl]-2-methyl-imidazo[4,5-c]quinolin-4-amine as a white powder. A portion of the white powder was dissolved in 5 mL of ethanol and combined with 0.5 mL of concentrated hydrochloric acid and the mixture was concentrated to dryness. Crystallization from ethyl acetate/hexanes gave 1-[(1S)-1-(ethoxymethyl)-2-methyl-propyl]-2-methyl-imidazo[4,5-c]quinolin-4-amine hydrochloride as white crystals. $^1H$ NMR (500 MHz, methanol-$d_4$) δ 8.55 (d, J=8.31 Hz, 0.5H), 8.21 (d, J=8.31 Hz, 0.5H), 7.81-7.86 (m, 1H), 7.76 (m, 1H), 7.61-7.68 (m, 1H), 5.23 (ddd, J=4.40, 8.56, 11.00 Hz, 0.5 H), 4.51-4.60 (m, 0.5H), 4.24-4.30 (m, 0.5H), 4.15-4.22 (m, 1H), 4.08-4.14 (m, 0.5H), 3.44-3.58 (m, 2H), 2.80 (m, 0.5H), 2.77 (s, 1.5H), 2.65 (m, 0.5H), 1.35 (d, J=6.48 Hz, 1.5H), 1.29 (d, 0.7=6.48 Hz, 1.5H), 1.03 (s, 3H), 0.77 (d, J=6.72 Hz, 1.5H), 0.75 (d, J=6.48 Hz, 1.5H).

Example 4

1-[(1R)-1-(ethoxymethyl)-2-methyl-propyl]-2-methyl-imidazo[4,5-c]quinolin-4-amine

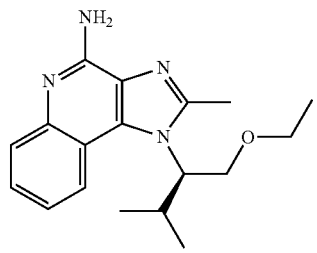 [SMILES: CCOC[C@@H](C(C)C)n1c(C)nc2c(N)nc3ccccc3c21]

1-[(1R)-1-(ethoxymethyl)-2-methyl-propyl]-2-methyl-imidazo[4,5-c]quinolin-4-amine was prepared from N4-[(1R)-1-(ethoxymethyl)-2-methyl-propyl]quinoline-3,4-diamine following the procedures described in Parts A-B of Example 3 and isolated as the hydrochloride salt. $^1H$ NMR (500 MHz, methanol-$d_4$) δ 8.55 (d, J=8.31 Hz, 0.5H), 8.21 (d, J=8.31 Hz, 0.5H), 7.80-7.87 (m, 1H), 7.76 (t, J=7.76 Hz, 1H), 7.59-7.69 (m, 1H), 5.23 (ddd, J=4.40, 8.56, 11.00 Hz, 0.5H), 4.51-4.60 (m, 0.5H), 4.23-4.30 (m, 0.5H), 4.15-4.22 (m, 1H), 4.08-4.14 (m, 0.5H), 3.43-3.59 (m, 2H), 2.85 (s, 1.5H), 2.80 (m, 0.5H), 2.77 (s, 1.5H), 2.65 (qd, J=6.56, 17.62 Hz, 0.5H), 1.35 (d, 0.7=6.48 Hz, 1.5H), 1.29 (d, J=6.48 Hz, 1.5H), 1.03 (t, J=6.97 Hz, 3H), 0.77 (d, J=6.72 Hz, 1.5H), 0.75 (d, J=6.48 Hz, 1.5H).

Example 5

(3R)-3-(4-aminoimidazo[4,5-c]quinolin-1-yl)-4-ethoxy-2-methyl-butan-2-ol

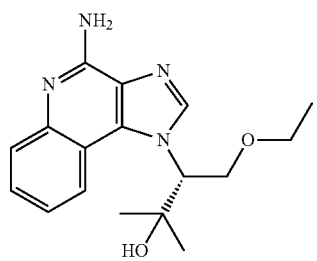 [SMILES: CCOC[C@@H](n1cnc2c(N)nc3ccccc3c21)C(C)(C)O]

Part A

A stirred solution of 3-tert-butyl 4-methyl (4R)-2,2-dimethyl-1,3-oxazolidine-3,4-dicarboxylate (2.59 g, 10.0 mmol, prepared according to the procedure of Williams, L, et al., *Tetrahedron*, 1996, 52(36), pages 11673-11694) was dissolved in 100 mL of anhydrous diethyl ether and cooled to −78° C. under an atmosphere of nitrogen. A 3.0 M solution of methyl magnesium bromide in diethyl ether (13.3 mL, 40 mmol) was slowly added to reaction mixture. After stirring for a few minutes, the reaction mixture was transferred to a 0° C. bath and stirring was continued for 1 hour. The reaction was then quenched by careful addition of a saturated solution of $NH_4Cl$. The layers were separated and the organic portion was washed successively with water and brine, dried over $MgSO_4$, filtered and concentrated under reduced pressure to give 2.19 g of tert-butyl (4R)-4-(1-hydroxy-1-methyl-ethyl)-2,2-dimethyl-oxazolidine-3-carboxylate as a colorless oil.

Part B

A stirred solution of tert-butyl (4R)-4-(1-hydroxy-1-methyl-ethyl)-2,2-dimethyl-oxazolidine-3-carboxylate (2.18 g, 8.42 mmol) dissolved in 20 mL of tetrahydrofuran was combined with 10 mL of IN hydrochloric acid solution and the mixture was heated to 40° C. for 3 hours. The reaction was cooled to ambient temperature, diluted with 50 mL of diethyl ether and washed successively with saturated sodium bicarbonate solution, water and brine. The organic portion was dried over $MgSO_4$, filtered and concentrated under reduced pressure to give 1.64 g of tert-butyl N-[(1R)-2-hydroxy-1-(hydroxymethyl)-2-methyl-propyl]carbamate as a colorless syrup.

Part C

A stirred solution of tert-butyl N-[(1R)-2-hydroxy-1-(hydroxymethyl)-2-methyl-propyl]carbamate (1.55 g, 7.08 mmol) dissolved in 15 mL of heptanes was combined with 2 g of 50% sodium hydroxide solution and diethyl sulfate (1.16 mL, 8.84 mmol) and 100 mg of tetrabutylammonium chloride hydrate. After stirring overnight, the reaction mixture was quenched with saturated $NH_4OH$ solution. After stirring for 2 hours, the reaction was diluted with 30 mL of heptanes and the layers were separated. The organic layer was washed successively with water (2×) and brine, dried over $Na_2SO_4$, filtered and concentrated under reduced pressure to give colorless oil. Purification by column chromatography ($SiO_2$, 10% ethyl acetate/hexanes-100% ethyl acetate) gave 1.01 g of tert-butyl N-[(1R)-1-(ethoxymethyl)-2-hydroxy-2-methyl-propyl]carbamate as a colorless oil.

Part D

A solution of tert-butyl N-[(1R)-1-(ethoxymethyl)-2-hydroxy-2-methyl-propyl]carbamate (1.01 g, 4.09 mmol) dissolved in 10 mL of ethanol was combined with 2 mL of concentrated hydrochloric acid and the mixture was heated to reflux overnight. The reaction mixture was then concentrated to dryness to give 0.75 g of (3R)-3-amino-4-ethoxy-2-methyl-butan-2-ol hydrochloride as a colorless syrup which solidified on standing.

Part E

A suspension of (3R)-3-amino-4-ethoxy-2-methyl-butan-2-ol hydrochloride (750 mg, 4.08 mmol) in 20 mL of dichloromethane was combined with 4-chloro-3-nitroquinoline (806 mg, 3.87 mmoL) and triethylamine (1.62 mL, 11.6 mmol) and the reaction mixture was stirred under an atmosphere of nitrogen overnight. The reaction mixture was concentrated to give a yellow solid. The solid was dissolved in 50 mL of ethyl acetate and washed with water (3×) and brine. The organic portion was dried over $Na_2SO_4$, filtered and concentrated to give a yellow solid. Purification by column chromatography ($SiO_2$, 10% ethyl acetate/hexanes-100% ethyl acetate) gave 1.16 g of (3R)-4-ethoxy-2-methyl-3-[(3-nitro-4-quinolyl)amino]butan-2-ol as a yellow solid.

Part F

A solution of (3R)-4-ethoxy-2-methyl-3-[(3-nitro-4-quinolyl)amino]butan-2-ol (1.16 g, 3.63 mmol) suspended in 30 mL acetonitrile was placed in a pressure bottle and combined with 120 mg of 3% platinum on carbon. The bottle was then shaken under an atmosphere of hydrogen (40 PSI) for 75 minutes. The reaction mixture was filtered through a pad of CELITE, rinsing with methanol, and the filtrate was concentrated under reduced pressure to give 1.04 g of (3R)-3-[(3-amino-4-quinolyl)amino]-4-ethoxy-2-methyl-butan-2-ol as a light yellow solid.

Part G

A solution of (3R)-3-[(3-amino-4-quinolyl)amino]-2-methyl-butan-2-ol (1.04 g, 3.60 mmol) dissolved in 30 mL of n-propyl acetate was combined with triethyl orthoformate (0.90 mL, 5.40 mmol) and 100 mg of pyridine hydrochloride and the mixture was heated to 90° C. overnight. The cooled reaction mixture was diluted with 50 mL of ethyl acetate and washed successively with saturated sodium bicarbonate solution, water and brine. The organic portion was dried over $Na_2SO_4$, filtered and concentrated to give a light brown foam. Purification by column chromatography ($SiO_2$, 2% methanol/chloroform-20% methanol/chloroform) gave 0.89 g of (3R)-4-ethoxy-3-imidazo[4,5-c]quinolin-1-yl-2-methyl-butan-2-ol as a light amber foam.

Part H

A solution of (3R)-4-ethoxy-3-imidazo[4,5-c]quinolin-1-yl-2-methyl-butan-2-ol (890 mg, 2.98 mmol) dissolved in 25 mL of dichloromethane was combined with 898 mg of MCPBA (57-86%) and stirred for 40 minutes. The reaction mixture was combined with 2% $Na_2CO_3$ solution and the layers were separated. The aqueous portion was further extracted with several portions of dichloromethane the combined organic portions were dried over $Na_2SO_4$, filtered and concentrated to give 0.77 g of an orange foam. The orange foam was dissolved in 25 mL of dichloromethane followed by the addition of concentrated $NH_4OH$ solution (10 mL) and para toluenesulfonyl chloride (625 mg, 3.28 mmol). After stirring for 45 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 10% CMA/chloroform-100% CMA) gave a light brown syrup. A portion of the syrup was dissolved in 2 mL of ethanol and treated with 0.5 mL of concentrated hydrochloric acid and concentrated to dryness. Crystallization from acetonitrile gave (3R)-3-(4-aminoimidazo[4,5-c]quinolin-1-yl)-4-ethoxy-2-methyl-butan-2-ol hydrochloride as colorless needles. $^1$H NMR (500 MHz, $D_2O$) δ 8.53 (s, 1H), 8.34 (d, J=8.44 Hz, 1H), 7.55-7.62 (m, 2H), 7.45 (ddd, J=2.51, 6.02, 8.47 Hz, 1H), 5.34 (dd, J=5.26, 9.17 Hz, 1H), 4.11-4.22 (m, 2H), 3.46 (m, 2H), 1.34 (s, 3H), 1.07 (s, 3H), 0.88 (t, J=7.03 Hz, 3H).

Example 6

(3 S)-3-(4-aminoimidazo[4,5-c]quinolin-1-yl)-4-ethoxy-2-methyl-butan-2-ol

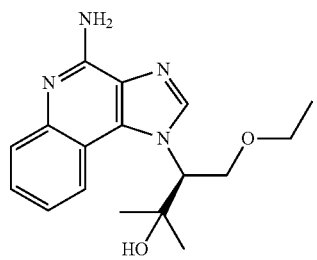 [SMILES: CCOC[C@H](n1cnc2c(N)nc3ccccc3c21)C(C)(C)O]

(3 S)-3-(4-aminoimidazo[4,5-c]quinolin-1-yl)-4-ethoxy-2-methyl-butan-2-ol was prepared from tert-butyl 4-methyl (4S)-2,2-dimethyl-1,3-oxazolidine-3,4-dicarboxylate following the procedures described in Parts A-H of Example 5 and isolated as the hydrochloride salt. $^1$H NMR (500 MHz, $D_2O$) δ 8.52 (s, 1H), 8.33 (d, J=8.44 Hz, 1H), 7.55-7.62 (m, 2H), 7.44 (ddd, J=2.14, 6.20, 8.28 Hz, 1H), 5.33 (dd, J=5.20, 9.11 Hz, 1H), 4.09-4.21 (m, 2H), 3.45 (m, 2H), 1.33 (s, 3H), 1.07 (s, 3H), 0.87 (t, 0.7=7.09 Hz, 3H).

Example 7

(3R)-3-(4-amino-2-methyl-imidazo[4,5-c]quinolin-1-yl)-4-ethoxy-2-methyl-butan-2-ol

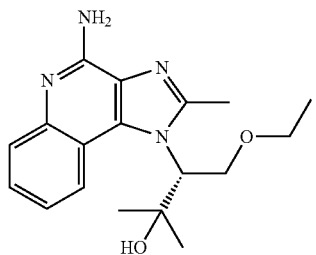 [SMILES: CCOC[C@@H](n1c(C)nc2c(N)nc3ccccc3c21)C(C)(C)O]

Part A

A solution of (3R)-4-ethoxy-3-imidazo[4,5-c]quinolin-1-yl-2-methyl-butan-2-ol (900 mg, 3.11 mmol) dissolved in 20 mL of n-propyl acetate was combined with triethyl orthoacetate (1.14 mL, 6.22 mmol) and 200 mg of pyridine hydrochloride and the mixture was heated to 103° C. overnight. The cooled reaction mixture was diluted with 50 mL of ethyl acetate and washed successively with saturated sodium bicarbonate solution, water and brine. The organic portion was dried over $Na_2SO_4$, filtered and concentrated to give a light brown foam. Purification by column chromatography ($SiO_2$, 1% methanol/chloroform-10% methanol/chloroform) gave 900 mg (3R)-4-ethoxy-2-methyl-3-(2-methylimidazo[4,5-c]quinolin-1-yl)butan-2-ol as a colorless syrup.

Part B

To a solution of (3R)-4-ethoxy-2-methyl-3-(2-methylimidazo[4,5-c]quinolin-1-yl)butan-2-ol (900 mg, 2.86 mmol) dissolved in 20 mL of dichloromethane was added 700 mg of MCPBA (80%) and the mixture was stirred for 1 hour. The reaction mixture was treated with 10% $Na_2CO_3$ solution and the layers were separated. The aqueous portion was further extracted with two additional portions of dichloromethane the combined organic layers were washed with brine, dried over $Na_2SO_4$, filtered and concentrated to give an amber foam. The amber foam was dissolved in 20 mL of dichloromethane followed by the addition of concentrated $NH_4OH$ solution (8 mL) and para toluenesulfonyl chloride (631 mg, 3.31 mmol). After stirring for 50 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 4% methanol/chloroform-15% methanol/chloroform) gave an amber foam. The foam was dissolved in 5 mL of ethanol and 0.3 mL of concentrated hydrochloric acid. The mixture was concentrated under reduced pressure to give a solid. Crystallization from ethyl acetate gave 263 mg of (3R)-3-(4-amino-2-methyl-imidazo[4,5-c]quinolin-1-yl)-4-ethoxy-2-methyl-butan-2-ol hydrochloride as yellow crystals. $^1$H NMR (500 MHz, methanol-$d_4$) δ 8.26-8.30 (m, 1H), 7.74 (dd, 0.7=1.16, 8.38 Hz, 1H), 7.50 (ddd, J=1.10, 7.12, 8.28 Hz, 1H), 7.35 (ddd, J=1.34, 7.06, 8.34 Hz, 1H), 5.60 (dd, J=5.56, 9.23 Hz, 1H), 4.43 (dd, J=9.23, 10.82 Hz, 1H), 4.25 (dd, J=5.50, 10.88 Hz, 1H), 3.49-3.60 (m, 2H), 2.94 (s, 3H), 1.57 (s, 3H), 1.06 (t, J=7.03 Hz, 3H), 1.01 (s, 3H).

Example 8

(3R)-3-(4-amino-2-ethyl-imidazo[4,5-c]quinolin-1-yl)-4-ethoxy-2-methyl-butan-2-ol

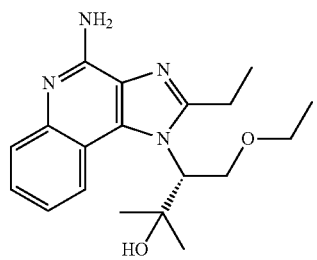 [SMILES: CCOC[C@@H](n1c(CC)nc2c(N)nc3ccccc3c21)C(C)(C)O]

Part A

A solution of (3R)-4-ethoxy-3-imidazo[4,5-c]quinolin-1-yl-2-methyl-butan-2-ol (842 mg, 2.91 mmol) dissolved in 20 mL of n-propyl acetate was combined with triethyl orthopropionate (1.17 mL, 5.82 mmol) and 200 mg of pyridine hydrochloride and the mixture was heated to 103° C. overnight. An additional 2.0 mL of triethyl orthopropionate was added and heating was continued for another day. The cooled reaction mixture was diluted with 50 mL of ethyl acetate and washed successively with saturated sodium bicarbonate solution, water and brine. The organic portion was dried over $Na_2SO_4$, filtered and concentrated to give a light brown foam. Purification by column chromatography ($SiO_2$, 1% methanol/chloroform-10% methanol/chloroform) gave as a colorless syrup. Crystallization from acetonitrile gave 519 mg of (3R)-4-ethoxy-3-(2-ethylimidazo[4,5-c]quinolin-1-yl)-2-methyl-butan-2-ol as colorless crystals.

Part B

To a solution of (3R)-4-ethoxy-2-methyl-3-(2-methylimidazo[4,5-c]quinolin-1-yl)butan-2-ol (519 mg, 1.59 mmol) dissolved in 20 mL of dichloromethane was added 359 mg of MCPBA (80%) and the mixture was stirred for 1 hour. The reaction mixture was treated with 10% $Na_2CO_3$ solution and the layers were separated. The organic layer was washed with brine and concentrated to give a light orange foam. The foam was dissolved in 20 mL of dichloromethane followed by the addition of concentrated $NH_4OH$ solution (5 mL) and para toluenesulfonyl chloride (333 mg, 1.75 mmol). After stirring for 1 hour, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 4% methanol/chloroform-20% methanol/chloroform) gave an orange foam. The foam was dissolved in 5 mL of ethanol and 0.3 mL of concentrated hydrochloric acid. The mixture was concentrated under reduced pressure to give a solid. Trituration from hot acetonitrile gave 398 mg of (3R)-3-(4-amino-2-ethyl-imidazo[4,5-c]quinolin-1-yl)-4-ethoxy-2-methyl-butan-2-ol hydrochloride as an amber solid. $^1$H NMR (500 MHz, methanol-$d_4$) δ 8.51 (d, 0.7=8.56 Hz, 1H), 7.85 (d, J=8.31 Hz, 1H), 7.72-7.78 (m, 1H), 7.64 (dt, J=1.22, 7.83 Hz, 1H), 5.62 (dd, J=5.44, 9.35 Hz, 1H), 4.39 (dd, J=9.48, 10.58 Hz, 1H), 4.26 (dd, J=5.38, 10.76 Hz, 1H), 3.63-3.73 (m, 1H), 3.47-3.61 (m, 2H), 3.11-3.22 (m, 1H), 1.58 (s, 3H), 1.52 (t, J=7.40 Hz, 3H), 1.06 (t, J=7.03 Hz, 3H), 1.04 (s, 3H).

Example 9

1-[(1S)-1-(ethoxymethyl)-2,2-dimethyl-propyl]imidazo[4,5-c]quinolin-4-amine

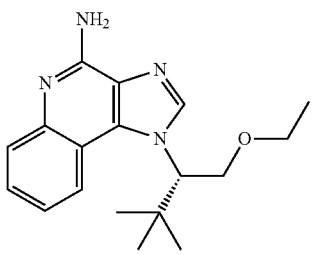 [SMILES: CCOC[C@@H](n1cnc2c(N)nc3ccccc3c21)C(C)(C)C]

Part A

A 250 mL 2-necked round bottom flask, equipped with an addition funnel containing iodine (5.08 g, 20.0 mmol) dissolved in 80 mL of tetrahydrofuran, was charged with NaBH$_4$ (1.82 g, 37.9 mmol). Tetrahydrofuran (50 mL) was added to the flask followed by L-tert-leucine (2.62 g, 20.0 mmol) and the mixture was stirred under nitrogen. The iodine solution was then added dropwise over a period of 30 minutes. The reaction mixture was then heated to reflux overnight. The reaction mixture was cooled to ambient temperature and carefully quenched with methanol. The reaction mixture was concentrated under reduced pressure to give a white paste which was dissolved in 30 mL of 20% KOH solution. The mixture was extracted with dichloromethane (3×20 mL) and the combined organic layers were dried over Na$_2$SO$_4$, filtered and concentrated under reduced pressure to give 2.22 g of (2S)-2'-amino-3,3-dimethyl-butan-1-ol as a colorless solid.

Part B

A solution of (2S)-2-amino-3,3-dimethyl-butan-1-ol (2.22 g, 19.0 mmol) dissolved in 30 mL of dichloromethane was combined with di-tert-butyl dicarbonate (4.14 g, 19.0 mmol) and triethylamine (2.91 mL, 20.9 mmol) and the reaction mixture was stirred overnight. The reaction mixture was then treated with 10% citric acid solution and the layers were separated. The organic portion was washed successively with 10% citric acid solution, water and brine, dried over Na$_2$SO$_4$, filtered and concentrated under reduced pressure to give 3.96 g of tert-butyl N-[(1S)-1-(hydroxymethyl)-2,2-dimethyl-propyl]carbamate as a white solid.

Part C

A stirred solution of tert-butyl N-[(1S)-1-(hydroxymethyl)-2,2-dimethyl-propyl]carbamate (2.06 g, 9.49 mmol) dissolved in 15 mL of heptanes was combined with 2 g of 50% NaOH solution and diethyl sulfate (1.55 mL, 11.9 mmol). Tetrabutylammonium chloride hydrate (100 mg) was then added to the reaction mixture. After stirring overnight, the reaction mixture was quenched with saturated NH$_4$OH solution. After stirring for 90 minutes, the reaction was diluted with 30 mL of heptanes and the layers were separated. The organic layer was washed successively with water (2×) and brine, dried over Na$_2$SO$_4$, filtered and concentrated under reduced pressure to give colorless oil. Purification by column chromatography (SiO$_2$, 10% ethyl acetate/hexanes) gave 1.43 g of tert-butyl N-[(1S)-1-(ethoxymethyl)-2,2-dimethyl-propyl]carbamate as a colorless oil.

Part D

A solution of tert-butyl N-[(1S)-1-(ethoxymethyl)-2,2-dimethyl-propyl]carbamate (1.43 g, 5.84 mmol) dissolved in 15 mL of ethanol was combined with 2.5 mL of concentrated hydrochloric acid and the mixture was heated to reflux for 3 hours. The reaction mixture was then concentrated to dryness to give 943 mg of (2S)-1-ethoxy-3,3-dimethyl-butan-2-amine hydrochloride as a white solid.

Part E

A suspension of (2S)-1-ethoxy-3,3-dimethyl-butan-2-amine hydrochloride (992 mg, 4.77 mmol) in 20 mL of dichloromethane was combined with 4-chloro-3-nitroquinoline (867 mg, 4.77 mmoL) and triethylamine (1.99 mL, 14.3 mmol) and the reaction mixture was stirred under an atmosphere of nitrogen overnight. The reaction mixture was concentrated to give a yellow solid. The solid was dissolved in 50 mL of ethyl acetate and washed with water (3×) and brine. The organic portion was dried over Na$_2$SO$_4$, filtered and concentrated to give a yellow solid. Purification by column chromatography (SiO$_2$, 10% ethyl acetate/hexanes-100% ethyl acetate) gave 1.26 g of N-[(1S)-1-(ethoxymethyl)-2,2-dimethyl-propyl]-3-nitro-quinolin-4-amine as a yellow solid.

Part F

A solution of N-[(1S)-1-(ethoxymethyl)-2,2-dimethyl-propyl]-3-nitro-quinolin-4-amine (1.26 g, 3.97 mmol) suspended in 25 mL acetonitrile was placed in a pressure bottle and combined with 100 mg of 3% platinum on carbon. The bottle was then shaken under an atmosphere of hydrogen (40 PSI) for 2 hours. The reaction mixture was filtered through a pad of CELITE and the filtrate was concentrated under reduced pressure to give 1.11 g of N4-[(1S)-1-(ethoxymethyl)-2,2-dimethyl-propyl]quinoline-3,4-diamine as an orange syrup.

Part G

A solution of N4-[(1S)-1-(ethoxymethyl)-2,2-dimethyl-propyl]quinoline-3,4-diamine (1.11 g, 3.87 mmol) dissolved in 20 mL of n-propyl acetate was combined with triethyl orthoformate (0.96 mL, 5.81 mmol) and 150 mg of pyridine hydrochloride and the mixture was heated to 90° C. overnight. The cooled reaction mixture was diluted with 50 mL of ethyl acetate and washed successively with saturated sodium bicarbonate solution, water and brine. The organic portion was dried over Na$_2$SO$_4$, filtered and concentrated to give a light brown foam. Purification by column chromatography (SiO$_2$, 1% methanol/chloroform-10% methanol/chloroform) gave 1.04 g of 1-[(1S)-1-(ethoxymethyl)-2,2-dimethyl-propyl]imidazo[4,5-c]quinoline as a light amber solid.

Part H

A solution of 1-[(1S)-1-(ethoxymethyl)-2,2-dimethyl-propyl]imidazo[4,5-c]quinoline (1.01 mg, 3.40 mmol) dissolved in 25 mL of dichloromethane was combined with 1.03 g of MCPBA (57-86%) and stirred for 50 minutes. The reaction mixture was treated with 2% Na$_2$CO$_3$ solution and the layers were separated. The aqueous portion was further extracted with several portions of dichloromethane the combined organic portions were dried over Na$_2$SO$_4$, filtered and concentrated to give 0.77 g of an orange foam.

The orange foam was dissolved in 25 mL of dichloromethane followed by the addition of concentrated NH$_4$OH solution (10 mL) and para toluenesulfonyl chloride (712 mg, 3.74 mmol). After stirring for 60 minutes, the reaction mixture was diluted with 25 mL of dichloromethane and washed with water (3×) and brine. The organic portion was dried over Na$_2$SO$_4$, filtered and concentrated under reduced pressure. Purification by column chromatography (SiO$_2$, 10% CMA/chloroform-33% CMA/chloroform) gave a light brown syrup. A portion of the syrup was dissolved in 2 mL of ethanol and treated with 0.5 mL of concentrated hydrochloric acid and concentrated to dryness. Crystallization from acetonitrile gave 1-[(1S)-1-(ethoxymethyl)-2,2-dimethyl-propyl]imidazo[4,5-c]quinolin-4-amine hydrochloride as colorless needles, $^1$H NMR (500 MHz, methanol-d$_4$) δ 8.48 (s, 1H), 8.36 (d, J=1.95 Hz, 1H), 7.72-7.76 (m, 1H), 7.49-7.54 (m, 1H), 7.33-7.38 (m, 1H), 5.31 (dd, J=3.67, 9.29 Hz, 1H), 4.18-4.25 (m, 1H), 4.09 (dd, J=3.42, 10.88 Hz, 1H), 3.43-3.56 (m, 2H), 1.07 (s, 9H), 1.04 (t, J=7.03 Hz, 3H).

Example 10

1-[(1R)-1-(ethoxymethyl)-2,2-dimethyl-propyl]imidazo[4,5-c]quinolin-4-amine

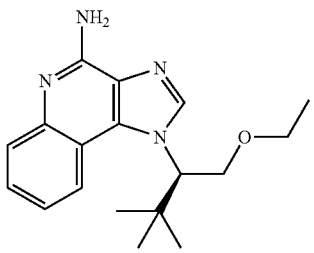 [SMILES: CCOC[C@H](n1cnc2c(N)nc3ccccc3c21)C(C)(C)C]

1-[(1R)-1-(ethoxymethyl)-2,2-dimethyl-propyl]imidazo[4,5-c]quinolin-4-amine was prepared from D-tert-leucine following the procedures described in Parts A-H of Example 9 and isolated as the hydrochloride salt. $^1$H NMR (500 MHz, methanol-d$_4$) δ 8.49 (s, 1H), 8.35-8.39 (m, 1H), 7.74 (dd, 0.7=1.04, 8.38 Hz, 1H), 7.53 (dt, 0.7=1.10, 7.70 Hz, 1H), 7.37 (dt, J=1.16, 7.67 Hz, 1H), 5.32 (dd, J=3.67, 9.29 Hz, 1H), 4.19-4.27 (m, 1H), 4.10 (dd, J=3.67, 10.88 Hz, 1H), 3.45-3.59 (m, 2H), 1.09 (s, 9H), 1.05 (t, J=7.03 Hz, 3H).

Example 11

1-[(1S)-1-(methoxymethyl)-2,2-dimethyl-propyl]imidazo[4,5-c]quinolin-4-amine

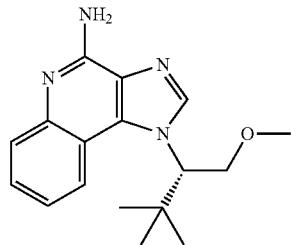 [SMILES: COC[C@@H](n1cnc2c(N)nc3ccccc3c21)C(C)(C)C]

Part A

To a stirred solution of tert-butyl N-[(1S)-1-(hydroxymethyl)-2,2-dimethyl-propyl]carbamate (1.80 g, 8.29 mmol) dissolved in 15 mL of heptanes were added 1.00 g of 50% NaOH solution and dimethyl sulfate (1.17 mL, 12.4 mmol). Tetrabutylammonium chloride hydrate (100 mg) was then added to the reaction mixture. After stirring overnight, the reaction mixture was then heated to 40° C. for 4 hours. The reaction was then cooled to ambient temperature and quenched by the addition of saturated NH$_4$OH solution. After stirring for 90 minutes, the reaction was diluted with 25 mL of heptanes and the layers were separated. The organic layer was washed successively with water (2×) and brine, dried over Na$_2$SO$_4$, filtered and concentrated under reduced pressure to give colorless oil. Purification by column chromatography (SiO$_2$, 10% ethyl acetate/hexanes) gave 0.99 g of tert-butyl N-[(1S)-1-(methoxymethyl)-2,2-dimethyl-propyl]carbamate as a colorless oil.

Part B

To a solution of tert-butyl N-[(1S)-1-(methoxymethyl)-2,2-dimethyl-propyl]carbamate (0.99 g, 4.29 mmol) dissolved in 10 mL of ethanol was added 3 mL of concentrated hydrochloric acid and the mixture was heated to reflux for 3 hours. The reaction mixture was then concentrated to dryness to give a white solid. Crystallization from acetonitrile gave 570 mg (2S)-1-methoxy-3,3-dimethyl-butan-2-amine hydrochloride as white needles.

Part C

To a suspension of (2S)-1-methoxy-3,3-dimethyl-butan-2-amine hydrochloride (570 mg, 3.40 mmol) in 20 mL of dichloromethane were added 4-chloro-3-nitroquinoline (700 mg, 3.37 mmoL) and triethylamine (1.40 mL, 10.1 mmol) and the reaction mixture was stirred under an atmosphere of nitrogen overnight. The reaction mixture was concentrated to give a yellow solid. The solid was dissolved in 50 mL of ethyl acetate and washed with water (3×) and brine. The organic portion was dried over Na$_2$SO$_4$, filtered and concentrated to give a yellow solid. Purification by column chromatography (SiO$_2$, 17% ethyl acetate/dichloromethane to 33% ethyl acetate/dichloromethane) gave 906 mg of N-[(1S)-1-(methoxymethyl)-2,2-dimethyl-propyl]-3-nitro-quinolin-4-amine as a yellow solid.

Part D

A solution of N-[(1S)-1-(methoxymethyl)-2,2-dimethyl-propyl]-3-nitro-quinolin-4-amine (906 mg, 2.99 mmol) dissolved in 15 mL acetonitrile was placed in a pressure bottle followed by the addition of 100 mg of 3% platinum on carbon. The bottle was then shaken under an atmosphere of hydrogen (40 PSI) for 2 hours. The reaction mixture was filtered through a pad of CELITE and the filtrate was concentrated under reduced pressure to give 816 mg of N4-[(1S)-1-(methoxymethyl)-2,2-dimethyl-propyl]quinoline-3,4-diamine as an orange solid.

Part E

To a solution of N4-[(1S)-1-(methoxymethyl)-2,2-dimethyl-propyl]quinoline-3,4-diamine (816 mg, 2.99 mmol) dissolved in 20 mL of n-propyl acetate were added triethyl orthoformate (0.75 mL, 4.48 mmol) and 150 mg of pyridine hydrochloride and the mixture was heated to 90° C. overnight. The cooled reaction mixture was diluted with 40 mL of ethyl acetate and washed successively with saturated sodium bicarbonate solution, water and brine. The organic portion was dried over Na$_2$SO$_4$, filtered and concentrated to give 703 mg of 1-[(1S)-1-(methoxymethyl)-2,2-dimethyl-propyl]imidazo[4,5-c]quinoline a yellow solid.

Part F

To a solution of 1-[(1S)-1-(methoxymethyl)-2,2-dimethyl-propyl]imidazo[4,5-c]quinoline (703 mg, 2.37 mmol) dissolved in 25 mL of dichloromethane was added 714 mg of MCPBA (57-86%) and the mixture was stirred for 50 minutes. The reaction mixture was treated with 2% Na$_2$CO$_3$ solution and the layers were separated. The aqueous portion was further extracted with several portions of dichloromethane. The combined organic portions were dried over Na$_2$SO$_4$, filtered and concentrated to give an orange foam. The orange foam was dissolved in 25 mL of dichloromethane followed by the addition of concentrated NH$_4$OH solution (9 mL) and para toluenesulfonyl chloride (497 mg, 2.61 mmol). After stirring rapidly for 60 minutes, the reaction mixture was diluted with 25 mL of dichloromethane and washed with water (3×) and brine. The organic portion was dried over Na$_2$SO$_4$, filtered and concentrated under reduced pressure. Purification by column chromatography (SiO$_2$, 10% CMA/chloroform-33% CMA/chloroform) gave an amber foam. Crystallization from ethyl acetate/hexanes gave 47 mg of 1-[(1S)-1-(methoxymethyl)-2,2-dimethyl-propyl]imidazo[4,5-c]quinolin-4-amine as off-white crystals. $^1$H NMR (500 MHz, methanol-d$_4$) δ 8.48 (s, 1H), 8.37 (dd, J=0.86, 8.44 Hz, 1H), 7.74 (dd, J=1.04, 8.38 Hz, 1H), 7.53 (ddd, J=1.22, 7.09, 8.31 Hz, 1H), 7.37 (ddd, J=1.28, 7.03, 8.31 Hz, 1H), 5.34 (dd, 0.7=3.73, 9.60 Hz, 1H), 4.20 (dd, J=9.72, 10.70 Hz, 1H), 4.06 (dd, J=3.67, 10.88 Hz, 1H), 3.33 (s, 3H), 1.10 (s, 9H).

Example 12

(2R)-2-(4-aminoimidazo[4,5-c]quinolin-1-yl)-1-ethoxy-3-ethyl-pentan-3-ol

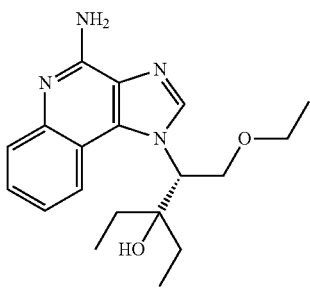 [SMILES: CCOC[C@@H](n1cnc2c(N)nc3ccccc3c21)C(O)(CC)CC]

Part A

A stirred solution of 3-tert-butyl 4-methyl (4R)-2,2-dimethyl-1,3-oxazolidine-3,4-dicarboxylate (3.68 g, 14.2 mmol) dissolved in 180 mL of anhydrous diethyl ether was cooled to −45° C. under an atmosphere of nitrogen. A 3.0 M solution of ethyl magnesium bromide in diethyl ether (18.9 mL, 56.8 mmol) was slowly added to reaction mixture. After stirring for a few minutes, the reaction mixture was allowed to warm to ambient temperature and stirring was continued for 6 hours. The reaction mixture was then cooled to 0° C. and quenched by careful addition of a saturated solution of NH$_4$Cl. The layers were separated and the organic portion was washed successively with water and brine, dried over MgSO$_4$, filtered and concentrated under reduced pressure to give 3.93 g of tert-butyl (4R)-4-(1-ethyl-1-hydroxy-propyl)-2,2-dimethyl-oxazolidine-3-carboxylate as a colorless oil.

Part B

To a stirred solution of tert-butyl (4R)-4-(1-ethyl-1-hydroxy-propyl)-2,2-dimethyl-oxazolidine-3-carboxylate (3.93 g, 13.7 mmol) dissolved in 40 mL of tetrahydrofuran was added 10 mL of 1N hydrochloric acid solution and the mixture was heated to 40° C. for 3 hours. The reaction mixture was cooled to ambient temperature, diluted with 40 mL of diethyl ether and washed successively with saturated sodium bicarbonate solution, water and brine. The organic portion was dried over MgSO$_4$, filtered and concentrated under reduced pressure to give 2.53 g of tert-butyl N-[(1R)-2-ethyl-2-hydroxy-1-(hydroxymethyl)butyl]carbamate as a white solid.

Part C

To a stirred solution of tert-butyl N-[(1R)-2-ethyl-2-hydroxy-1-(hydroxymethyl)butyl]carbamate (2.53 g, 10.2 mmol) dissolved in 20 mL of heptanes were added 2.0 g of 50% NaOH solution and diethylsulfate (1.67 mL, 12.8 mmol). Tetrabutylammonium chloride hydrate (250 mg) was then added. After stirring overnight, the reaction mixture was quenched with saturated NH$_4$OH solution. After stirring for 2 hours, the reaction was diluted with 30 mL of heptanes and the layers were separated. The organic layer was washed successively with water (2×) and brine, dried over Na$_2$SO$_4$, filtered and concentrated under reduced pressure to give colorless oil. Purification by column chromatography (SiO$_2$, 10% ethyl acetate/hexanes-50% ethyl acetate/hexanes) gave 1.79 g of tert-butyl N-[(1R)-1-(ethoxymethyl)-2-ethyl-2-hydroxy-butyl]carbamate as a colorless oil.

Part D

A solution of tert-butyl N-[(1R)-1-(ethoxymethyl)-2-ethyl-2-hydroxy-butyl]carbamate (1.79 g, 6.51 mmol) dissolved in 10 mL of ethanol followed by the addition of 1.5 mL of concentrated hydrochloric acid and the mixture was heated to reflux for 2 hours. The reaction mixture was then concentrated several times from ethanol to give 1.01 g of (2R)-2-amino-1-ethoxy-3-ethyl-pentan-3-ol hydrochloride as a pink syrup.

Part E

To a suspension of (2R)-2-amino-1-ethoxy-3-ethyl-pentan-3-ol hydrochloride (1.01 g, 4.77 mmol) in 20 mL of dichloromethane were added 4-chloro-3-nitroquinoline (992 mg, 4.77 mmoL) and triethylamine (1.99 mL, 14.3 mmol) and the reaction mixture was stirred under an atmosphere of nitrogen overnight. The reaction mixture was concentrated to give a yellow solid. The solid was dissolved in 50 mL of ethyl acetate and washed with water (3×) and brine. The organic portion was dried over Na$_2$SO$_4$, filtered and concentrated to give a yellow solid. Purification by column chromatography (SiO$_2$, 10% ethyl acetate/hexanes-33% ethyl acetate/hexanes) gave 1.33 g of (2R)-1-ethoxy-3-ethyl-2-[(3-nitro-4-quinolyl)amino]pentan-3-ol as a yellow solid.

Part F

A solution of (2R)-1-ethoxy-3-ethyl-2-[(3-nitro-4-quinolyl)amino]pentan-3-ol (1.33 g, 3.83 mmol) dissolved in 30 mL acetonitrile was placed in a pressure bottle followed by the addition of 120 mg of 3% platinum on carbon. The bottle was then shaken under an atmosphere of hydrogen (40 PSI) for 2 hours. The reaction mixture was filtered through a pad of CELITE and the filtrate was concentrated under reduced pressure to give 1.21 g of (2R)-2-[(3-amino-4-quinolyl)amino]-1-ethoxy-3-ethyl-pentan-3-ol as an orange oil.

Part G

To a solution of (2R)-2-[(3-amino-4-quinolyl)amino]-1-ethoxy-3-ethyl-pentan-3-ol (1.21 g, 3.82 mmol) dissolved in 30 mL of n-propyl acetate were added triethyl orthoformate (1.26 mL, 7.63 mmol) and 200 mg of pyridine hydrochloride and the mixture was heated to 90° C. overnight. The cooled reaction mixture was diluted with 50 mL of ethyl acetate and washed successively with saturated sodium bicarbonate solution, water and brine. The organic portion was dried over Na$_2$SO$_4$, filtered and concentrated to give a light brown foam. Purification by column chromatography (SiO$_2$, 1% methanol/chloroform-10% methanol/chloroform) gave 1.01 g of (2R)-1-ethoxy-3-ethyl-2-imidazo[4,5-c]quinolin-1-yl-pentan-3-ol as a mauve foam.

Part H

To a solution of (2R)-1-ethoxy-3-ethyl-2-imidazo[4,5-c]quinolin-1-yl-pentan-3-ol (993 mg, 3.04 mmol) dissolved in 20 mL of dichloromethane was added 686 mg of MCPBA (57-86%) and the mixture was stirred for 1 hour. The reaction mixture was treated with a 10% $Na_2CO_3$ solution and the layers were separated. The aqueous portion was further extracted with two additional portions of dichloromethane the combined organic layers were dried over $Na_2SO_4$, filtered and concentrated to give an orange foam. The orange foam was dissolved in 20 mL of dichloromethane followed by the addition of concentrated $NH_4OH$ solution (6 mL) and para toluenesulfonyl chloride (637 mg, 3.34 mmol). After stirring for 1 hour, the reaction mixture was diluted with 25 mL of dichloromethane and washed with water (3×) and brine. The organic portion was dried over $Na_2SO_4$, filtered and concentrated under reduced pressure. Purification by column ($SiO_2$, 2% methanol/chloroform-20% methanol/chloroform) gave an orange foam. The orange foam was dissolved in 2 mL of ethanol and 0.5 mL of concentrated hydrochloric acid. The mixture was concentrated under reduced pressure to give a solid. Crystallization from acetonitrile gave 367 mg of (2R)-2-(4-aminoimidazo[4,5-c]quinolin-1-yl)-1-ethoxy-3-ethyl-pentan-3-ol hydrochloride as colorless needles. $^1$H NMR (500 MHz, methanol-$d_4$) δ 8.79 (s, 1H), 8.51 (d, 0.7=8.07 Hz, 1H), 7.81-7.85 (m, 1H), 7.76 (dt, J=0.98, 7.76 Hz, 1H), 7.63 (dt, J=1.22, 7.76 Hz, 1H), 5.40 (dd, J=3.85, 9.35 Hz, 1H), 4.19-4.25 (m, 1H), 4.10-4.18 (m, 1H), 3.54 (qd, J=7.03, 9.49 Hz, 1H), 3.43 (qd, J=7.04, 9.45 Hz, 1H), 1.88 (q, J=7.34 Hz, 2H), 1.19-1.37 (m, 2H), 1.07 (t, J=7.46 Hz, 3H), 0.97 (t, J=7.03 Hz, 3H), 0.76 (t, J=7.46 Hz, 3H).

Example 13

(3R,4S)-3-(4-aminoimidazo[4,5-c]quinolin-1-yl)-4-ethoxy-2-methyl-pentan-2-ol

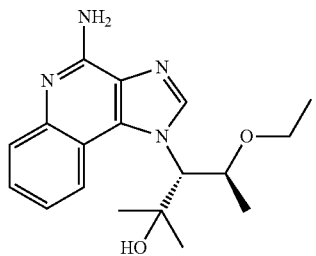 [SMILES: CCO[C@@H](C)[C@@H](n1cnc2c(N)nc3ccccc3c21)C(C)(C)O]

Part A

A 1-L round bottom flask was charged with 250 mL of anhydrous methanol and cooled in an ice water bath. Thionyl chloride (8.03 ml, 110 mmol) was added over a few minutes to the stirred methanol followed by the addition of D-threonine (11.9 g, 100 mmol). The reaction mixture was removed from the ice bath and then heated to reflux for 3 hours. The reaction mixture was concentrated under reduced pressure to give 16.9 g of methyl (2R,3S)-2-amino-3-hydroxy-butanoate hydrochloride as a white solid.

Part B

A mixture of methyl (2R,3S)-2-amino-3-hydroxy-butanoate hydrochloride (16.9 g, 100 mmol) suspended in 250 mL of dichloromethane was combined with di-tert-butyl dicarbonate (19.6 g, 90 mmol) and triethylamine (39 mL, 280 mmol) and the reaction mixture was stirred overnight. The reaction mixture was then treated with 5% aqueous $NaH_2PO_4$ solution and the layers were separated. The organic portion was washed successively with saturated sodium bicarbonate solution, 10% citric acid solution, water and brine, dried over $Na_2SO_4$, filtered and concentrated under reduced pressure to give 18.1 g of methyl (2R,3S)-2-(tert-butoxycarbonylamino)-3-hydroxy-butanoate as a colorless oil.

Part C

A solution of methyl (2R,3S)-2-(tert-butoxycarbonylamino)-3-hydroxy-butanoate dissolved (18.0 g, 77.3 mmol) in 80 mL of toluene was combined with 2,2-dimethoxypropane (13.2 mL, 108 mmol) and camphor sulfonic acid (500 mg). The reaction flask was equipped with a Dean-Stark trap and the mixture was heated to reflux under an atmosphere of nitrogen. After several milliliters of distillate was collected an additional 5 mL of 2,2-dimethoxypropane was added and heating was continued overnight. The reaction mixture was cooled and combined with a saturated sodium bicarbonate solution and 100 mL of diethyl ether. The layers were separated and the organic portion was washed sequentially with water and brine, dried over $MgSO_4$, filtered and concentrated to give O3-tert-butyl O4-methyl (4R,5S)-2,2,5-trimethyloxazolidine-3,4-dicarboxylate 18.0 g of an amber liquid.

Part D

A stirred solution of O3-tert-butyl O4-methyl (4R,5S)-2,2,5-trimethyloxazolidine-3,4-dicarboxylate (13.8 g, 50.5 mmol) dissolved in 400 mL of anhydrous diethyl ether was cooled to −10° C. under an atmosphere of nitrogen. A 3.0 M solution of methyl magnesium bromide in diethyl ether (67 mL, 202 mmol) was slowly added to the reaction mixture. After stirring for a few minutes, the reaction mixture was allowed to warm to ambient temperature and stirring was continued for 3.5 hours. The reaction was then cooled in an ice bath and quenched by careful addition of a saturated solution of $NH_4Cl$. The layers were separated and the organic portion was washed successively with water and brine, dried over $MgSO_4$, filtered and concentrated under reduced pressure to give 13.0 g of tert-butyl (4R,5S)-4-(1-hydroxy-1-methyl-ethyl)-2,2,5-trimethyl-oxazolidine-3-carboxylate as a golden oil.

Part E

A stirred solution of tert-butyl (4R,5S)-4-(1-hydroxy-1-methyl-ethyl)-2,2,5-trimethyl-oxazolidine-3-carboxylate (13.0 g, 47.6 mmol) dissolved in 100 mL of ethanol was combined with 15 mL of concentrated hydrochloric acid and the mixture was heated to reflux for 2 hours. The reaction mixture was then concentrated from toluene and acetonitrile to give 8.04 g of (3R,4S)-3-amino-2-methyl-pentane-2,4-diol hydrochloride as a light purple syrup.

Part F

A solution of (3R,4S)-3-amino-2-methyl-pentane-2,4-diol hydrochloride (8.04 g, 47.6 mmol) in 250 mL of dichloromethane was combined with 4-chloro-3-nitroquinoline (9.04 g, 45.2 mmoL) and triethylamine (19.9 mL, 143 mmol) and the reaction mixture was stirred under an atmosphere of nitrogen overnight. The reaction mixture was concentrated to give a yellow solid. The solid was triturated in 250 mL of hot water and filtered to give a fluffy yellow solid. Crystallization from acetonitrile gave 9.80 g of (3R,4S)-2-methyl-3-[(3-nitro-4-quinolyl)amino]pentane-2,4-diol as yellow crystals.

Part G

A solution of (3R,4S)-2-methyl-3-[(3-nitro-4-quinolyl)amino]pentane-2,4-diol (7.75 g, 25.4 mmol) dissolved in 20 mL of anhydrous pyridine was combined with tert-butyldimethylsilyl triflate (50% solution in toluene, 8.4 mL, 30.5 mmol) and dimethylaminopyridine (310 mg, 2.54 mmol) and the mixture was heated to 80° C. for 3 days. The reaction mixture was partitioned between dichloromethane and water and the layers were separated. The organic portion was washed successively with 1N hydrochloric acid solution, water and brine, dried over $Na_2SO_4$, filtered and concentrated to give 11.1 g of (3R,4S)-4-[tert-butyl(dimethyl)silyl]oxy-2-methyl-3-[(3-nitro-4-quinolyl)amino]pentan-2-ol as a yellow solid.

Part H

A solution of (3R,4S)-4-[tert-butyl(dimethyl)silyl]oxy-2-methyl-3-[(3-nitro-4-quinolyl)amino]pentan-2-ol (11.1 g, 26.5 mmol) dissolved in 200 mL acetonitrile was placed in a pressure bottle and combined with 500 mg of 3% platinum on carbon. The bottle was then shaken under an atmosphere of hydrogen (40 PSI) for 24 hours. The reaction mixture was filtered through a pad of CELITE, rinsing with acetonitrile, and the filtrate was concentrated under reduced pressure to give 10.3 g of (3R,4S)-3-[(3-amino-4-quinolyl)amino]-4-[tert-butyl(dimethyl)silyl]oxy-2-methyl-pentan-2-ol as a dark red syrup.

Part I

A solution of (3R,4S)-3-[(3-amino-4-quinolyl)amino]-4-[tert-butyl(dimethyl)silyl]oxy-2-methyl-pentan-2-ol (10.3 g, 26.5 mmol) dissolved in 250 mL of n-propyl acetate was combined with triethyl orthoformate (13.2 mL, 79.4 mmol) and 250 mg of pyridine hydrochloride and the mixture was heated to 90° C. overnight. The reaction mixture was then treated with an additional 3 mL of triethylorthoformate and heating was continued for 4 hours. The cooled reaction mixture was diluted with 100 mL of ethyl acetate and washed successively with saturated sodium bicarbonate solution, water and brine. The organic portion was dried over $Na_2SO_4$, filtered and concentrated to give a brown syrup. The brown syrup was dissolved in 200 mL of toluene, combined with 100 mg of camphor sulfonic acid, and then heated to reflux for 4 hours. The cooled reaction mixture was washed successively with saturated sodium bicarbonate solution, water and brine. The organic portion was dried over $Na_2SO_4$, filtered and concentrated to give 10 g of crude (3R,4S)-4-[tert-butyl(dimethyl)silyl]oxy-3-imidazo[4,5-c]quinolin-1-yl-2-methyl-pentan-2-ol as a brown syrup.

Part J

A solution of crude (3R,4S)-4-[tert-butyl(dimethyl)silyl]oxy-3-imidazo[4,5-c]quinolin-1-yl-2-methyl-pentan-2-ol (10 g) dissolved in 100 mL of tetrahydrofuran was combined with 34 mL of a 1.0 N solution of tetrabutylammonium fluoride in tetrahydrofuran and the mixture was stirred overnight. The reaction mixture was diluted with 200 mL of chloroform and washed successively with saturated sodium bicarbonate solution, water and brine (3×). The organic portion was dried over $Na_2SO_4$, filtered and concentrated under reduced pressure. Purification by column chromatography ($SiO_2$, 1% methanol/chloroform-10% methanol/chloroform) gave 3.90 g of (3R,4S)-3-imidazo[4,5-c]quinolin-1-yl-2-methyl-pentane-2,4-diol a yellow foam.

Part K

A solution of (3R,4S)-3-imidazo[4,5-c]quinolin-1-yl-2-methyl-pentane-2,4-diol (285 mg, 1.0 mmol) dissolved in 5 mL of anhydrous tetrahydrofuran was combined with potassium tert-butoxide (168 mg, 1.5 mmol) and iodoethane (96 microliters, 1.2 mmol) and the mixture was stirred under an atmosphere of nitrogen overnight. The reaction was quenched by the addition of saturated sodium bicarbonate solution and then diluted with ethyl acetate. The layers were separated and the organic portion washed successively with water and brine. The organic portion was dried over $Na_2SO_4$, filtered and concentrated under reduced pressure. Purification by column chromatography ($SiO_2$, 1% methanol/chloroform-10% methanol/chloroform) gave 238 mg of (3R,4S)-4-ethoxy-3-imidazo[4,5-c]quinolin-1-yl-2-methyl-pentan-2-ol as an amber foam.

Part L

A solution of (3R,4S)-4-ethoxy-3-imidazo[4,5-c]quinolin-1-yl-2-methyl-pentan-2-ol (238 mg, 0.76 mmol) dissolved in 5 mL of dichloromethane was treated with 163 mg of MCPBA (80%) and stirred for 50 minutes. The reaction mixture was treated with 10% $Na_2CO_3$ solution and the layers were separated. The aqueous portion was further extracted with two portions of dichloromethane. The combined organic portions were washed with brine, dried over $Na_2SO_4$, filtered and concentrated to give an orange foam. The orange foam was dissolved in 3 mL of dichloromethane and combined with 1 mL of concentrated $NH_4OH$ solution and para toluenesulfonyl chloride (159 mg, 0.84 mmol). After stirring for 50 minutes, the reaction mixture was diluted with 10 mL of dichloromethane and washed with water (3×) and brine. The organic portion was dried over $Na_2SO_4$, filtered and concentrated under reduced pressure. Purification by column chromatography ($SiO_2$, 10% methanol/chloroform saturated with $NH_4OH$) gave an amber foam. The foam was dissolved in 2 mL of ethanol and treated with 0.2 mL of concentrated hydrochloric acid and then concentrated to dryness. Crystallization from propyl acetate gave 76 mg of (3R,4S)-3-(4-aminoimidazo[4,5-c]quinolin-1-yl)-4-ethoxy-2-methyl-pentan-2-ol hydrochloride as yellow crystals. $^1$H NMR (500 MHz, methanol-$d_4$) δ 8.73 (s, 1H), 8.61 (d, 0.7=7.95 Hz, 1H), 7.81-7.85 (m, 1H), 7.76 (dt, J=0.98, 7.76 Hz, 1H), 7.62 (ddd, J=1.22, 7.21, 8.44 Hz, 1H), 5.21 (d, 0.7=2.93 Hz, 1H), 4.49 (dq, J=2.87, 6.22 Hz, 1H), 3.82 (qd, J=6.99, 9.09 Hz, 1H), 3.57 (qd, J=7.05, 9.05 Hz, 1H), 1.52 (s, 3H), 1.34 (t, J=7.03 Hz, 3H), 1.28 (s, 3H), 1.00 (d, J=6.24 Hz, 3H).

Example 14

1-[(1R)-1-(4-aminoimidazo[4,5-c]quinolin-1-yl)-2-ethoxy-ethyl]cyclopentanol

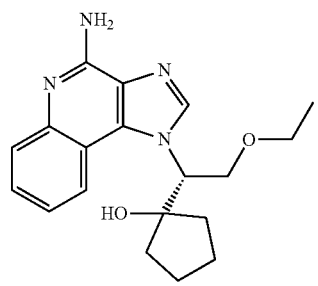 [SMILES: CCOC[C@@H](n1cnc2c(N)nc3ccccc3c21)C1(O)CCCC1]

Part A

A stirred solution of 3-tert-butyl 4-methyl (4?)-2,2-dimethyl-1,3-oxazolidine-3,4-dicarboxylate (7.10 g, 27.4 mmol, prepared according to the procedure of Williams, L, et al., *Tetrahedron*, 1996, 52(36), pages 11673-11694) was dissolved in 300 mL of anhydrous diethyl ether and cooled to −20° C. under an atmosphere of nitrogen. A 1.0 M solution of allyl magnesium bromide in diethyl ether (100 mL, 100 mmol) was slowly added to the reaction mixture over 15 minutes. The reaction mixture was then allowed to warm to ambient temperature and stirring was continued for 2.5 hours. The reaction mixture was then transferred to a 0° C. bath and was quenched by careful addition of a saturated solution of $NH_4Cl$. The layers were separated and the organic portion was washed successively with water and brine, dried over $MgSO_4$, filtered and concentrated under reduced pressure to give a colorless oil. Purification by column chromatography ($SiO_2$, 5% ethyl acetate/hexanes-10% ethyl acetate/hexanes) gave 6.11 g of tert-butyl (4R)-4-(1-allyl-1-hydroxy-but-3-enyl)-2,2-dimethyl-oxazolidine-3-carboxylate as a colorless oil.

Part B

To a stirred solution of tert-butyl (4R)-4-(1-allyl-1-hydroxy-but-3-enyl)-2,2-dimethyl-oxazolidine-3-carboxylate (5.10 g, 16.4 mmol) dissolved in 50 mL of tetrahydrofuran was added 20 mL of 1N hydrochloric acid solution and the mixture was heated to 40° C. for 90 minutes. The reaction was cooled to ambient temperature, diluted with 100 mL of diethyl ether and washed successively with saturated sodium bicarbonate solution, water and brine. The organic portion was dried over $MgSO_4$, filtered and concentrated under reduced pressure to give 3.95 g of tert-butyl N-[(1R)-2-allyl-2-hydroxy-1-(hydroxymethyl)pent-4-enyl]carbamate as a white solid.

Part C

To a stirred solution of tert-butyl N-[(1R)-2-allyl-2-hydroxy-1-(hydroxymethyl)pent-4-enyl]carbamate (3.90 g, 14.4 mmol) dissolved in 30 mL of heptanes were added with 3.2 g of 50% NaOH solution and diethylsulfate (2.35 mL, 18.0 mmol) and the reaction mixture was heated to 50° C. under an atmosphere of nitrogen. Tetrabutylammonium chloride hydrate (193 mg) was then added and stirring was continued for 90 minutes. The reaction mixture was then cooled to ambient temperature and quenched with saturated $NH_4OH$ solution. After stirring for 2 hours, the reaction was diluted with 30 mL of heptanes and the layers were separated. The organic layer was washed successively with water (2×) and brine, dried over $Na_2SO_4$, filtered and concentrated under reduced pressure to give colorless oil. Purification by column chromatography ($SiO_2$, 5% ethyl acetate/hexanes-20% ethyl acetate/hexanes) gave 2.72 g of tert-butyl N-[(1R)-2-allyl-1-(ethoxymethyl)-2-hydroxy-pent-4-enyl]carbamate as a colorless oil.

Part D

A round bottom flask was charged with 3-bromopyridine (0.5 mL) and benzylidene[1,3-bis(2,4,6-trimethylphenyl)-2-imidazolidinylidene] dichloro(tricyclohexylphosphine)ruthenium (84 mg) and the reactants were stirred for 5 minutes. Hexane (15 mL) was added to the flask and the mixture was filtered to provide a light green solid. The solid was added to a stirred solution of tert-butyl N-[(1R)-2-allyl-1-(ethoxymethyl)-2-hydroxy-pent-4-enyl]carbamate (1.21 g, 4.05 mmol) in 50 mL of dry dichloromethane that had been degassed with a stream of nitrogen. The reaction was heated at 45° C. and stirred for 15 minutes under an atmosphere of nitrogen. Air was bubbled through the reaction mixture and then the reaction mixture was concentrated under reduced pressure. Purification by column chromatography ($SiO_2$, 29% ethyl acetate/hexanes) gave 0.93 g of tert-butyl N-[(1R)-2-ethoxy-1-(1-hydroxycyclopent-3-en-1-yl)ethyl]carbamate as a light brown syrup.

Part E

A solution of tert-butyl N-[(1R)-2-ethoxy-1-(1-hydroxycyclopent-3-en-1-yl)ethyl]carbamate (1.67 g, 6.16 mmol) suspended in 20 mL methanol was placed in a pressure bottle and combined with 50 mg of 10% palladium on carbon. The bottle was then shaken under an atmosphere of hydrogen (40 PSI) for 90 minutes. The reaction mixture was filtered through a pad of CELITE, rinsing with methanol, and the filtrate was concentrated under reduced pressure. Purification by column chromatography ($SiO_2$, 10% ethyl acetate/hexanes to 50% ethyl acetate/hexanes) gave 1.21 g of tert-butyl N-[(1R)-2-ethoxy-1-(1-hydroxycyclopentyl)ethyl]carbamate as a colorless syrup.

Part F

A solution of tert-butyl N-[(1R)-2-ethoxy-1-(1-hydroxycyclopentyl)ethyl]carbamate (1.21 g, 4.43 mmol) dissolved in 15 mL of ethanol was combined with 2 mL of concentrated hydrochloric acid and the mixture was heated to reflux for 90 minutes. The reaction mixture was then concentrated to dryness to give 0.92 g of 1-[(1R)-1-amino-2-ethoxy-ethyl]cyclopentanol hydrochloride as a mauve colored syrup.

Part G

A solution of 1-[(1R)-1-amino-2-ethoxy-ethyl]cyclopentanol hydrochloride (0.91 g, 5.06 mmol) in 20 mL of dichloromethane was combined with 4-chloro-3-nitroquinoline (1.05 g, 5.06 mmoL) and triethylamine (2.11 mL, 15.2 mmol) and the reaction mixture was stirred under an atmosphere of nitrogen overnight. The reaction mixture was concentrated to give a yellow solid. The solid was dissolved in 60 mL of ethyl acetate and washed with water (3×) and brine. The organic portion was dried over $Na_2SO_4$, filtered and concentrated to give a yellow solid. Purification by column chromatography ($SiO_2$, 1% methanol/chloroform to 5% methanol/chloroform) gave 1.20 g of 1-[(1R)-2-ethoxy-1-[(3-nitro-4-quinolyl)amino]ethyl]cyclopentanol as a yellow solid.

Part H

A solution of 1-[(1R)-2-ethoxy-1-[(3-nitro-4-quinolyl)amino]ethyl]cyclopentanol (1.20 g, 3.47 mmol) suspended in 30 mL acetonitrile was placed in a pressure bottle and combined with 100 mg of 3% platinum on carbon. The bottle was then shaken under an atmosphere of hydrogen (40 PSI) for 90 minutes. The reaction mixture was filtered through a pad of CELITE, rinsing with methanol, and the filtrate was concentrated under reduced pressure to give 1.10 g of 1-[(1R)-1-[(3-amino-4-quinolyl)amino]-2-ethoxy-ethyl]cyclopentanol as a light yellow solid.

Part I

A solution of 1-[(1R)-1-[(3-amino-4-quinolyl)amino]-2-ethoxy-ethyl]cyclopentanol (1.10 g, 3.49 mmol) dissolved in 30 mL of n-propyl acetate was combined with triethyl orthoformate (1.90 mL, 11.4 mmol) and 50 mg of pyridine hydrochloride and the mixture was heated to 96° C. overnight. The cooled reaction mixture was washed successively with saturated sodium bicarbonate solution, water and brine. The organic portion was dried over $Na_2SO_4$, filtered and concentrated to give a light brown foam. Purification by column chromatography ($SiO_2$, 1% methanol/chloroform-10% methanol/chloroform) gave 993 mg of 1-[(1R)-2-ethoxy-1-imidazo[4,5-c]quinolin-1-yl-ethyl]cyclopentanol as a light brown foam.

Part J

A solution of 1-[(1R)-2-ethoxy-1-imidazo[4,5-c]quinolin-1-yl-ethyl]cyclopentanol (993 mg, 3.06 mmol) dissolved in 25 mL of dichloromethane was combined with 657 mg of MCPBA (80%) and stirred for 50 minutes. The reaction mixture was then combined with 10 mL of concentrated NH₄OH solution and para toluenesulfonyl chloride (642 mg, 3.37 mmol). After stirring for 45 minutes, the reaction mixture was diluted with 25 mL of dichloromethane and washed with water (3×) and brine. The organic portion was dried over $Na_2SO_4$, filtered and concentrated under reduced pressure. Purification by column chromatography ($SiO_2$, 5% methanol/chloroform saturated with NH₄OH) gave a light brown foam. Crystallization from ethyl acetate/hexanes gave 287 mg of 1-[(1R)-1-(4-aminoimidazo[4,5-c]quinolin-1-yl)-2-ethoxy-ethyl]cyclopentanol as gray crystals. $^1$H NMR (500 MHz, methanol-d₄) δ 8.60 (s, 1H), 8.34 (d, J=7.70 Hz, 1H), 7.74 (dd, J=1.04, 8.38 Hz, 1H), 7.53 (t, J=7.40 Hz, 1H), 7.35 (t, J=7.40 Hz, 1H), 5.38 (dd, J=4.28, 8.80 Hz, 1H), 4.15-4.26 (m, 2H), 3.50-3.59 (m, 1H), 3.42-3.50 (m, 1H), 1.86-2.05 (m, 3H), 1.69-1.84 (m, 2H), 1.53-1.63 (m, 2H), 1.24-1.31 (m, 1H), 1.05-1.06 (m, 1H), 1.03 (t, J=7.03 Hz, 3H).

Cytokine Induction in Human Cells

Whole blood was obtained from healthy human donors and collected by venipuncture into vacutainer tubes or syringes containing EDTA. Human peripheral blood mononuclear cells (PBMC) were purified from the whole blood by density gradient centrifugation. Histopaque 1077 (15 mL, Sigma, St. Louis, MO) was transferred to 6×50 mL sterile polypropylene conical tubes. The Histopaque was overlayed with 15-25 mL of blood diluted 1:2 in Hank's Balanced Salts Solution (HBSS) (Gibco, Life Technologies, Grand Island, NY). The tubes were then centrifuged at 1370 rpm for 30 minutes at 20° C., with no brake (400×g, GH 3.8A Rotor).

The interface (buffy coat) containing the PBMC was collected and placed in a new sterile 50 mL conical polypropylene centrifuge tube. The PBMC were mixed with an equal volume of HBSS (about 20 mL from the interface and about 20 mL of HBSS), and then centrifuged at 1090 rpm, 10 minutes, 20° C., with brake (270×g, GH 3.8A Rotor). After completing centrifugation, the cells were resuspended in 2-3 mL ACK Red blood cell lysis buffer (ammonium chloride potassium solution, Gibco, Life Technologies) and incubated for 2-5 minutes at 20° C. Next, HBSS (40 mL) was added to the cells, and the sample was centrifuged at 270×g for 10 minutes at 20° C. The supernatant was decanted, and the cell pellet was resuspended in 5 mL AIM V Medium (Gibco, Life Technologies). Cell aggregates and debris were removed by filtering the cell solution through a BD Falcon 70 micron nylon cell strainer (BD Biosciences, San Jose, CA).

The number of viable cells was determined by counting with a Miltenyi FACS instrument (Miltenyi Biotec Inc., San Diego, CA) or by using a hemocytometer. For determining cell viability with a hemocytometer, the cells were diluted 1/10 in 0.4% trypan blue and HBSS (specifically, 50 microliter of trypan blue+40 microliter of HBSS+10 microliter of cell solution were added to a microfuge tube and mixed). Ten microliters of the diluted cells were then applied to the hemocytometer, and the number of viable PBMC were determined by microscopy.

The PBMC sample was then resuspended in 96-well plates at a concentration of 8×10⁵ cells/well in 0.1 mL of AIM-V medium. Each compound was solubilized in dimethyl sulfoxide (DMSO) to create a 3 mM stock solution. The stock solution was then further diluted with AIM-V medium to prepare the serial dilutions. The diluted compound (100 microliters) was then transferred to the PBMCs to produce testing sets with final compound concentrations of either 30, 10, 3.3, 1.1, 0.37, 0.12, 0.04, 0.01 micromolar (testing set A); 30, 10, 3.3, 1.1, 0.37, 0.12, 0.04 micromolar (testing set B); 100, 33.3, 11.1, 3.7, 1.2, 0.4 micromolar (testing set C); or 3.0, 1.0, 0.33, 0.11, 0.037, 0.012, 0.004, 0.0014 micromolar (testing set D). The plates also had both positive and negative controls. The negative control wells contained only AIM-V medium with no example compound. The positive control wells contained a control set of imiquimod serially diluted to concentrations of either 30, 10, 3.3, 1.1, 0.37, 0.12, 0.04, 0.01 micromolar (control set A); 30, 10, 3.3, 1.1, 0.37, 0.12, 0.04 micromolar (control set B); 100, 33.3, 11.1, 3.7, 1.2, 0.4 micromolar (control set C); or 3.0, 1.0, 0.33, 0.11, 0.037, 0.012, 0.004, 0.0014 micromolar (control set D). The concentrations used in the control set were selected to match the concentrations used in the testing set. The plates were then cultured at 37° C. 15% $CO_2$ for 21-24 hours. Cell-free supernatants were harvested by centrifuging the 96-well plates at 2100 rpm, 23° C. for 10 minutes. Approximately 160 microliters of the supernatant were then stored in a NUNC 96-well plate, covered with the compression cap and stored at −80° C. until the cytokine analysis was done.

IFN-alpha cytokine levels (picograms/mL) were measured by ELISA (human IFN-alpha, pan specific, Mabtech, Cincinnati, OH). IFN-gamma and TNF-alpha levels (picograms/mL) were measured by multiplex bead assay (magnetic beads, R & D Systems, Minneapolis, MN) according to the manufacturer's instructions.

The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (pictograms/mL) that was at least 2× greater than that observed with the negative control wells. The results are presented in Table 22. The "designations "≤0.01", "≤0.04", "≤0.4", "≤0.014" indicate that cytokine induction was observed at the lowest concentration of compound evaluated in the assay (i.e. the lowest of compound in testing sets A, B, C, or D).

TABLE 22

Cytokine Induction

| | MEC to Induce Cytokine (micromolar) | | |
|---|---|---|---|
| Compound | IFN-alpha | IFN-gamma | TNF-alpha |
| Example 1 | ≤0.04 | ≤0.04 | ≤0.04 |
| Example 2 | 3.3 | >30 | 3.3 |
| Example 3 | 0.37 | 1.1 | 0.37 |
| Example 4 | 10 | >30 | 10 |
| Example 5 | 0.12 | 0.12 | 0.04 |
| Example 6 | >100 | >100 | >100 |
| Example 7 | 0.12 | 0.37 | not tested |
| Example 8 | 10 | 3.3 | not tested |
| Example 9 | 0.004 | 0.012 | 0.004 |
| Example 10 | 3.0 | 3.0 | 3.0 |
| Example 11 | ≤0.4 | ≤0.4 | ≤0.4 |
| Example 12 | 0.04 | 0.12 | not tested |
| Example 13 | 3.3 | 10 | 10 |
| Example 14 | not tested | not tested | not tested |

TLR Activation and Specificity

HEK-BLUE-hTLR7 or hTLR8 reporter cells were obtained from InvivoGen, San Diego, CA According to the manufacturer's description, these reporter cells were prepared by co-transfection of HEK293 cells with an inducible secreted embryonic alkaline phosphatase (SEAP) reporter gene and either the human TLR7 or TLR8 gene. The SEAP reporter gene was placed under the control of an IFN-β minimal promoter fused to five NF-κB and AP-1-binding sites. In the presence of a TLR ligand, activation of NF-κB and AP-1 occurs, resulting in a corresponding increase in SEAP levels.

Parental HEK293 cells (null), which expressed the inducible SEAP reporter, but did not express TLR7 or TLR8, were obtained from InvivoGen and served as the negative control in the assay.

In the assay, the HEK cells were grown and maintained using standard cell culture techniques in a growth medium that contained Dulbecco's Modified Eagle Medium (ThermoFisher Scientific Incorporated, Waltham, MA) supplemented with 1% penicillin/streptomycin and 10% heat-inactivated Gibco fetal bovine serum (ThermoFisher Scientific). Each compound was solubilized in DMSO to create a 3 mM stock solution. The stock solution was then further diluted with the growth medium to prepare serial dilutions. Each test compound was tested at a concentration of 30, 10, 3.3, 1.1, 0.37, 0.12, 0.04, and 0.01 micromolar using a 96-well format with $5 \times 10^4$ cells and 200 microliters of growth medium per well.

For each compound, hTLR7, hTLR8, and their respective null control HEK cells were screened. DMSO serially diluted into the growth medium served as the vehicle control. Cell culture supernatants containing the SEAP reporter were collected after an incubation period of 16-20 hours in a cell culture incubator (37° C. and 5% $CO_2$), and either analyzed immediately or stored at −80° C. SEAP levels were measured using the colorimetric enzyme assay (QUANTI-BLUE (InvivoGen) according to manufacturer's instructions.

The data was analyzed to determine the minimum effective concentration (MEC) for each compound at which activation was observed in the assay. Specifically, the minimum effective concentration of each compound (micromolar) was determined as the lowest concentration of the compound that produced a SEAP expression response at least 2× greater than that observed with the vehicle control wells. The results are presented in Table 23. The "designation "≤0.01" indicates that TLR activation was observed at the lowest concentration of compound evaluated in the assay.

TABLE 23

TLR Activation

| Compound | MEC to Produce TLR Activation (micromolar) | |
| --- | --- | --- |
|  | TLR 7 | TLR 8 |
| Example 1 | 0.12 | 30 |
| Example 2 | 3.3 | >30 |
| Example 3 | 1.1 | 30 |
| Example 4 | >30 | >30 |
| Example 5 | ≤0.01 | 3.3 |
| Example 6 | >30 | >30 |
| Example 7 | 0.37 | 1.1 |
| Example 8 | 10 | 10 |
| Example 9 | ≤0.01 | 30 |
| Example 10 | 30 | >30 |
| Example 11 | 0.04 | >30 |
| Example 12 | 0.04 | 30 |
| Example 13 | 3.3 | 10 |
| Example 14 | 0.04 | 30 |

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of Formula (II), or salt thereof:

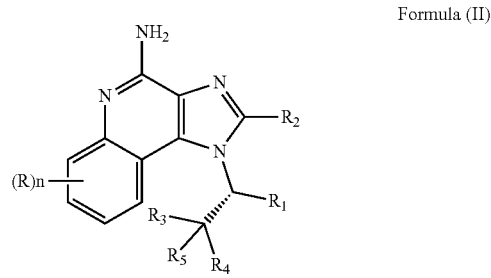

Formula (II)

wherein:

n is an integer of 0 or 1;

R is selected from the group consisting of halogen, hydroxy, alkyl, alkoxy, and —C(O)—O-alkyl;

$R_1$ is —X—O—Y where X is a $C_{1-3}$alkylene and Y is a $C_{1-3}$alkyl;

$R_2$ is selected from the group consisting of hydrogen, methyl, ethyl, n-propyl, n-butyl, —CH$_2$OCH$_3$, —CH$_2$OCH$_2$CH$_3$, and —CH$_2$CH$_2$OCH$_3$;

$R_3$ is a $C_{1-4}$alkyl, $R_4$ is a $C_{1-4}$alkyl, or $R_3$ and $R_4$ are combined to form a ring of 3-7 carbon atoms optionally having one oxygen atom in the ring; and $R_5$ is —H, —CH$_3$, —F, or —OH.

2. The compound or salt of claim 1, wherein R is selected from the group consisting of halogen, hydroxy, —C$_{1-12}$alkyl, —C$_{1-12}$alkoxy, and —C(O)—O—C$_{1-10}$alkyl.

3. The compound or salt of claim 1, wherein n is 0.

4. The compound or salt of claim 1, wherein $R_1$ is —X—O—Y where X is —CH$_2$—, —CH$_2$CH$_2$—, or —CH(CH$_3$)— and Y is a $C_{1-3}$alkyl.

5. The compound or salt of claim 1, wherein Y is —CH$_3$ or —CH$_2$CH$_3$.

6. The compound or salt of claim 1, wherein $R_3$ is a $C_{1-4}$alkyl.

7. The compound or salt of claim 1, wherein $R_4$ is a $C_{1-4}$alkyl.

8. The compound or salt of claim 1, wherein $R_3$ and $R_4$ are combined to form a ring of 3-7 carbon atoms optionally having one oxygen atom in the ring.

9. The compound or salt of claim 1, wherein $R_1$ is —X—O—Y where X is —CH$_2$— or —CH(CH$_3$)— and Y is —CH$_3$ or —CH$_2$CH$_3$; $R_2$ is selected from the group consisting of hydrogen, methyl, and ethyl; $R_3$ is a $C_{1-4}$alkyl; $R_4$ is a $C_{1-4}$alkyl; $R_5$ is —H, —CH$_3$, or —OH; and n is 0.

10. The compound or salt of claim 9, wherein the compound is (3R)-3-(4-aminoimidazo[4,5-c]quinolin-1-yl)-4-ethoxy-2-methyl-butan-2-ol.

11. The compound or salt of claim 9, wherein the compound is (3R)-3-(4-amino-2-methyl-imidazo[4,5-c]quinolin-1-yl)-4-ethoxy-2-methyl-butan-2-ol.

12. The compound or salt of claim 9, wherein the compound is (3R)-3-(4-amino-2-ethyl-imidazo[4,5-c]quinolin-1-yl)-4-ethoxy-2-methyl-butan-2-ol.

13. The compound or salt of claim 9, wherein the compound is 1-[(1S)-1-(ethoxymethyl)-2,2-dimethyl-propyl]imidazo[4,5-c]quinolin-4-amine.

14. The compound or salt of claim 9, wherein the compound is 1-[(1S)-1-(methoxymethyl)-2,2-dimethyl-propyl]imidazo[4,5-c]quinolin-4-amine.

15. The compound or salt of claim 9, wherein the compound is (2R)-2-(4-aminoimidazo[4,5-c]quinolin-1-yl)-1-ethoxy-3-ethyl-pentan-3-ol.

16. The compound or salt of claim 9, wherein the compound is (3R,4S)-3-(4-aminoimidazo[4,5-c]quinolin-1-yl)-4-ethoxy-2-methyl-pentan-2-ol.

17. The compound or salt of claim 1, wherein $R_1$ is —X—O—Y where X is —$CH_2$— or —$CH(CH_3)$— and Y is —$CH_3$ or —$CH_2CH_3$; $R_2$ is selected from the group consisting of hydrogen, methyl, and ethyl; $R_3$ and $R_4$ are combined to form a ring of 3-7 carbon atoms optionally having one oxygen atom in the ring; $R_5$ is —H, —$CH_3$, or —OH; and n is 0.

18. The compound or salt of claim 17, wherein the compound is 1-[(1R)-1-(4-aminoimidazo[4,5-c]quinolin-1-yl)-2-ethoxy-ethyl]cyclopentanol.

19. A pharmaceutical composition comprising an effective amount of a compound or salt of claim 1 in combination with a pharmaceutically acceptable carrier.

20. The pharmaceutical composition of claim 19, further comprising an antigen.

21. A method of inducing cytokine biosynthesis in a human or animal comprising administering an effective amount of a compound or salt of claim 1 to the human or animal.

22. A method of treating a neoplastic disease in a human or animal by administering an effective amount of a compound or salt of claim 1 to the human or animal.

\* \* \* \* \*